US008003665B2

(12) United States Patent
Kruk et al.

(10) Patent No.: US 8,003,665 B2
(45) Date of Patent: *Aug. 23, 2011

(54) SALTS AND POLYMORPHS OF A POTENT ANTIDIABETIC COMPOUND

(75) Inventors: Henry T. Kruk, San Jose, CA (US); Lawrence R. McGee, Pacifica, CA (US); Bing Yang, Redwood City, CA (US)

(73) Assignee: Amgen Inc., Thousand Oaks, CA (US)

( * ) Notice: Subject to any disclaimer, the term of this patent is extended or adjusted under 35 U.S.C. 154(b) by 772 days.

This patent is subject to a terminal disclaimer.

(21) Appl. No.: 11/807,208

(22) Filed: May 24, 2007

(65) Prior Publication Data

US 2007/0293536 A1 Dec. 20, 2007

Related U.S. Application Data

(63) Continuation of application No. 10/956,251, filed on Oct. 1, 2004, now Pat. No. 7,223,761.

(60) Provisional application No. 60/508,470, filed on Oct. 3, 2003.

(51) Int. Cl.
*A61K 31/04* (2006.01)

(52) U.S. Cl. ........................................ 514/312

(58) Field of Classification Search ................ 546/159, 546/162; 514/312
See application file for complete search history.

(56) References Cited

U.S. PATENT DOCUMENTS

| | | | |
|---|---|---|---|
| 2,407,309 A | 9/1946 | Lott et al. | |
| 3,034,955 A | 5/1962 | Frick et al. | |
| 3,174,901 A | 3/1965 | Sterne | |
| 3,669,966 A | 6/1972 | Ambrogi et al. | |
| 3,674,843 A | 7/1972 | Shen et al. | |
| 3,686,192 A | 8/1972 | Moore et al. | |
| 4,003,734 A | 1/1977 | Johnston | |
| 4,013,621 A | 3/1977 | Knell | |
| 4,061,642 A | 12/1977 | Fleckenstein et al. | |
| 4,062,950 A | 12/1977 | Frommer et al. | |
| 4,218,237 A | 8/1980 | Nishiyama et al. | |
| 4,289,876 A | 9/1981 | Algieri et al. | |
| 4,499,304 A | 2/1985 | Gabrielsen et al. | |
| 4,549,901 A | 10/1985 | James | |
| 4,565,568 A | 1/1986 | Johnston et al. | |
| 4,572,912 A | 2/1986 | Yoshioka et al. | |
| 4,577,028 A | 3/1986 | Martin et al. | |
| 4,670,045 A | 6/1987 | Ehr et al. | |
| 4,731,090 A | 3/1988 | Boger et al. | |
| 4,756,739 A | 7/1988 | Fuss et al. | |
| 4,851,419 A | 7/1989 | Cox | |
| 4,866,079 A | 9/1989 | Boger et al. | |
| 4,900,751 A | 2/1990 | Cox | |
| 4,946,854 A | 8/1990 | Maienfisch et al. | |
| 4,952,235 A | 8/1990 | Andree et al. | |
| 4,987,141 A | 1/1991 | Bushell et al. | |
| 5,008,276 A | 4/1991 | Clough et al. | |
| 5,070,096 A | 12/1991 | Mohrs et al. | |
| 5,093,340 A | 3/1992 | Mohrs et al. | |
| 5,143,937 A | 9/1992 | Lang et al. | |
| 5,151,428 A | 9/1992 | Sakamoto et al. | |
| 5,202,336 A | 4/1993 | Mohrs et al. | |
| 5,204,354 A | 4/1993 | Chakravarty et al. | |
| 5,250,549 A | 10/1993 | Yoshino et al. | |
| 5,304,532 A | 4/1994 | Munro et al. | |
| 5,360,810 A | 11/1994 | Hayase et al. | |
| 5,444,036 A | 8/1995 | Iwasaki et al. | |
| 5,514,696 A | 5/1996 | Murugesan et al. | |
| 5,545,669 A | 8/1996 | Adams et al. | |
| 5,610,320 A | 3/1997 | Yoshino et al. | |
| 5,624,937 A | 4/1997 | Reel et al. | |
| 5,643,914 A | 7/1997 | Daines | |
| 5,684,195 A | 11/1997 | Huang et al. | |
| 5,716,993 A | 2/1998 | Ozaki et al. | |
| 5,780,483 A | 7/1998 | Widdowson et al. | |
| 5,814,646 A | 9/1998 | Heinz et al. | |
| 5,880,136 A | 3/1999 | Duggan et al. | |
| 5,981,586 A | 11/1999 | Pershadsingh et al. | |
| 5,990,126 A | 11/1999 | Park | |
| 6,022,897 A | 2/2000 | Evans et al. | |
| 6,028,052 A | 2/2000 | Heyman et al. | |
| 6,200,995 B1 | 3/2001 | De la Brouse-Elwood et al. | |
| 6,214,850 B1 | 4/2001 | Evans et al. | |
| 6,262,112 B1 | 7/2001 | Mittendorf et al. | |
| 6,294,559 B1 | 9/2001 | Smith | |
| 6,348,474 B1 | 2/2002 | Kayakiri et al. | |
| 6,353,011 B1 | 3/2002 | Pershadsingh et al. | |
| 6,369,075 B1 | 4/2002 | Ruggeri et al. | |

(Continued)

FOREIGN PATENT DOCUMENTS

CH 592 411 10/1977

(Continued)

OTHER PUBLICATIONS

U.S. Appl. No. 60/141,672, filed Jun. 30, 1999, McGee et al. U.S. Appl. No. 60/201,613, filed May 3, 2000, Jaen et al.
Badilescu, I., Chemical Abstracts, vol. 67, No. 9, Aug. 28, 1967, Columbus, Ohio, United States; abstract No. 43516y, p. 4076; XP002099084; "Synthesis of some N-aryl- and N,N-dialkyl-p-chloro-benzensulfonamides" Rev.Chim., 17(11):705-6 (1966).
Baguley et al., Database accession No. 108:179602, Database Chemabs 'Online!, RN 106831-10-1 CAPLUS, Eur. J. Cancer Clin. Oncol., 24(2):205-210 (1988).
Burmistrov et al., Database accession No. 115:8165, Database Chemabs 'Online!, RNs 98187-76-9 CAPLUS, 134284-4-5 CAPLUS, Ah,. Org. Khim, 26(9):1995-1998 (1990).
Burmistrov et al., Database accession No. 122:132338, Database Chemabs 'Online!, RN 134284-40-5 CAPLUS, Zh. Org. Khim, 30(5):744-747 (1994).

(Continued)

*Primary Examiner* — D Seaman
(74) *Attorney, Agent, or Firm* — Jones Day

(57) ABSTRACT

Salts and polymorphs of a compound useful in the treatment of inflammatory and metabolic conditions and diseases are provided herein. In particular, the invention provides salts and polymorphs of a compound which modulates the expression and/or function of a peroxisome proliferator-activated receptor. The salts and polymorphs are useful for the treatment or prevention of conditions and disorders associated with energy homeostasis such as type II diabetes, lipid metabolism, adipocyte differentiation and inflammation.

2 Claims, 9 Drawing Sheets

U.S. PATENT DOCUMENTS

Figure 1:
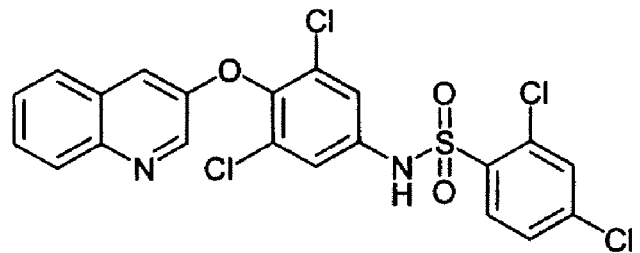

| | | |
|---|---|---|
| 6,403,607 B1 | 6/2002 | Hidaka et al. |
| 6,403,656 B1 | 6/2002 | Rivier et al. |
| 6,469,054 B1 | 10/2002 | Mittendorf et al. |
| 6,472,779 B2 | 10/2002 | Hwang et al. |
| 6,545,050 B1 | 4/2003 | Mittendorf et al. |
| 6,583,157 B2 | 6/2003 | McGee et al. |
| 6,586,475 B1 | 7/2003 | Kato et al. |
| 6,620,827 B2 | 9/2003 | de la Brouse-Elwood et al. |
| 6,653,309 B1 | 11/2003 | Saunders et al. |
| 6,653,332 B2 | 11/2003 | Saunders et al. |
| 6,770,648 B2 | 8/2004 | McGee et al. |
| 7,041,691 B1 | 5/2006 | McGee et al. |
| 7,132,546 B2 | 11/2006 | Kato et al. |
| 7,223,761 B2 * | 5/2007 | Kruk et al. ............ 514/252.04 |
| 7,439,242 B2 | 10/2008 | Houze et al. |
| 7,601,841 B2 | 10/2009 | McGee et al. |
| 7,626,033 B2 | 12/2009 | McGee et al. |
| 2003/0088103 A1 | 5/2003 | Houze et al. |
| 2003/0171399 A1 | 9/2003 | McGee et al. |
| 2004/0048891 A1 | 3/2004 | Kato et al. |
| 2004/0176409 A1 | 9/2004 | McGee et al. |
| 2004/0248882 A1 | 12/2004 | McGee et al. |
| 2004/0259918 A1 | 12/2004 | Jaen et al. |
| 2005/0250820 A1 | 11/2005 | Chen |
| 2006/0035928 A1 | 2/2006 | Jaen et al. |
| 2006/0264481 A1 | 11/2006 | Chen |
| 2009/0221635 A1 | 9/2009 | McGee et al. |
| 2010/0113522 A1 | 5/2010 | McGee et al. |

FOREIGN PATENT DOCUMENTS

| | | |
|---|---|---|
| DE | 3632329 | 3/1988 |
| EP | 0 069 585 | 1/1983 |
| EP | 0 148 730 | 7/1985 |
| EP | 0 261 539 A2 | 9/1987 |
| EP | 0 261 539 | 3/1988 |
| EP | 0 306 222 | 3/1989 |
| EP | 0 749 751 | 12/1996 |
| EP | 0 778 267 | 6/1997 |
| EP | 0 472 053 | 6/1998 |
| EP | 0 855 391 | 7/1998 |
| FR | 2773075 A1 | 7/1999 |
| GB | 2373725 | 10/2002 |
| JP | 55-79369 | 6/1980 |
| JP | 64-6245 | 1/1989 |
| JP | 9-255656 | 9/1997 |
| WO | 95/01326 | 1/1995 |
| WO | 95/33461 | 12/1995 |
| WO | 96/09294 | 3/1996 |
| WO | 96/15118 | 5/1996 |
| WO | 97/30677 | 8/1997 |
| WO | 97/00857 | 9/1997 |
| WO | 97/31907 | 9/1997 |
| WO | 97/36579 | 10/1997 |
| WO | 98/02437 | 1/1998 |
| WO | 98/27081 | 6/1998 |
| WO | WO 98/29120 | 7/1998 |
| WO | 98/37061 | 8/1998 |
| WO | WO 98/39006 | 9/1998 |
| WO | 98/50029 | 11/1998 |
| WO | 98/50030 | 11/1998 |
| WO | 99/00372 | 1/1999 |
| WO | 99/06378 | 2/1999 |
| WO | 99/10320 | 3/1999 |
| WO | 99/38845 | 8/1999 |
| WO | 99/50237 | 10/1999 |
| WO | 99/55663 | 11/1999 |
| WO | 00/10967 | 3/2000 |
| WO | 00/10968 | 3/2000 |
| WO | 00/12073 | 3/2000 |
| WO | 00/12623 | 3/2000 |
| WO | 00/17202 | 3/2000 |
| WO | 00/31021 | 6/2000 |
| WO | 01/00579 | 1/2001 |
| WO | 01/30343 | 5/2001 |
| WO | 01/60807 | 8/2001 |
| WO | 01/83427 | 8/2001 |
| WO | 01/70723 | 9/2001 |
| WO | 01/82916 | 11/2001 |
| WO | 01/87860 | 11/2001 |
| WO | 01/87861 | 11/2001 |
| WO | 01/87862 | 11/2001 |
| WO | 01/95906 | 12/2001 |
| WO | 02/00611 | 1/2002 |
| WO | 02/08188 | 1/2002 |
| WO | WO 02/00633 | 1/2002 |
| WO | 02/13812 | 2/2002 |
| WO | 02/13864 | 2/2002 |
| WO | 02/14291 | 2/2002 |
| WO | 02/17901 | 3/2002 |
| WO | 02/18355 | 3/2002 |
| WO | 02/26729 | 4/2002 |
| WO | 02/26737 | 4/2002 |
| WO | 02/28832 | 4/2002 |
| WO | 02/28857 | 4/2002 |
| WO | 02/30860 | 4/2002 |
| WO | 02/30863 | 4/2002 |
| WO | 02/30884 | 4/2002 |
| WO | 02/30895 | 4/2002 |
| WO | 02/40020 | 5/2002 |
| WO | 02/46161 | 6/2002 |
| WO | 02/49626 | 6/2002 |
| WO | 02/051397 | 7/2002 |
| WO | 02/051820 | 7/2002 |
| WO | 02/053546 | 7/2002 |
| WO | 02/059098 | 8/2002 |
| WO | 02/060434 | 8/2002 |
| WO | 02/062772 | 8/2002 |
| WO | 02/062774 | 8/2002 |
| WO | 02/062798 | 8/2002 |
| WO | 02/062799 | 8/2002 |
| WO | 02/064094 | 8/2002 |
| WO | 02/066028 | 8/2002 |
| WO | 02/072003 | 9/2002 |
| WO | 02/074291 | 9/2002 |
| WO | 02/080913 | 10/2002 |
| WO | 02/081454 | 10/2002 |
| WO | 02/090882 | 11/2002 |
| WO | 02/092084 | 11/2002 |
| WO | 02/092590 | 11/2002 |
| WO | WO 2005/033074 | 4/2005 |
| WO | WO 2005/086904 | 9/2005 |

OTHER PUBLICATIONS

Cain et al., "Potential antitumor agents. 14. Acridylmethanesulfonanilides," J. Med. Chem. 17(9):922-930 (1974).

Chaturvedi et al., "Antibacterial studies of 7-(α-substituted sulfonamido)methyl- and 7-(α-substituted sulfonamido)phenyl-8-hydroxyquinolines," Journal of the Indian Chemical Society 61(2):175-176 (1984) (Abstract. Chem. Abstract Accession No. 101:87311).

Collins et al., "N-(2-Benzoylphenyl)-L-tyrosine PPARγ agonists. 2. Structure-activity relationship and optimization of the phenyl alkyl ether moiety," J. Med. Chem. 41(25):5037-5054 (1998).

Denny et al., Database accession No. 96:79437, Database Chemabs 'Online!, RNs 80260-24-8 CAPLUS, 80260-260 CAPLUS, J. Med. Chem., 25(3):276-315 (1982).

Dumas, Chemical Abstracts 131:336969, abstract of Bioorg Med Chem Legg, 9(17):2531-2536 (1999).

Forman et al., "15-Deoxy-$\Delta^{12-14}$-Prostagladin $J_2$ Is a Ligand for the Adipocyte Determination Factor PPARγ," Cell, 83:803-812 (1995).

Jiang et al., "PPAR-γ agonists inhibit production of monocyte inflammatory cytokines," Nature 391:82-86 (1998).

Lehmann et al., "Peroxisome Proliferator-activated Receptors α and γ Are Activated by Indomethacin and Other Non-steroidal Anti-inflammatory Drugs," The Journal of Biological Chemistry, 272(6):3406-3410 (1997).

Lehmann, J. et al., "An antidiabetic Thiazolidinedione is a high affinity ligand for peroxisome proliferator-activated receptor γ (PPARγ)" J. Biol. Chem 270(22):12953-12956 (1995).

Merck Index, THE, 10th Ed., Windholz et al., eds. Merck & Co., Inc., Rahway, NJ., pp. 849-850, Abstract 5792 (1983).

Mysyk et al., Database accession No. 92:163637, Database Chemabs 'Online!, RN 73320-75-9 CAPLUS, Zh. Org. Khim, 15(12): 2499-2502 (1979).

Pieper et al., Database accession No. 112:138679, Database Chemabs "Online!, RN 101513-48-8 CAPLUS, Arzneim.-Forsch., 39(9):1073-1080 (1989).

Ricote et al., "The peroxisome proliferator-activated receptor-γ is a negative regulator of macrophage activation," Nature 391:79-82 (1998).

Sarul, et al., Database accession No. 103:123106, Database Chemabs 'Online!, RN 98187-77-0 CAPLUS, Latv. Psr Ainat. Akad. Vestis, Kim. Ser., 2:225-228 (1985).

Sebe et al., Database accession No. 117:214517, Database Chemabs 'Online!, RNs 144206-02-0 CAPLUS, 144232-65-5 CAPLUS, Rev. Chim, 43(5-6):222-225 (1992).

Spiegelman, B.M., "PPAR-γ: adipogenic regulator and thiazolidinedione receptor," Diabetes 47:507-514 (1998).

Wilson et al., "The Structure-Activity Relationship between Peroxisome Proliferator-Activated Receptor γ Agonism and the Antohyperglycemic Activity of Thiazolidinediones," J. med. Chem., 39:665-668 (1996).

Willson et al., "The PPARs: from orphan receptors to drug discovery" J. Med. Chem. 43(4):527-550 (2000).

Wollweber et al., Database accession No. 101:151540, Database Chemabs 'Online!, RN 92114-63-1 CAPLUS, Arzneim.-Forsch., 34(5): 531-542 (1984).

Zaitseva et al., Database accession No. 86:43377, Database Chemabs 'Online!, RN 61381-98-4 CAPLUS, Zh. Org. Khim, 12(9):1987-1992 (1976).

Akahoshi et al., "Rapid induction of peroxisome proliferator-activated receptor gamma expression in human monocytes by monosodium urate monohydrate crystals," Arthritis Rheum. 48(1):231-239 (2003).

Arora et al., "The low dose combination of fenofibrate and rosiglitazone halts the progression of diabetes-induced experimental nephropathy," Eur J Pharmacol.25;636(1-3):137-144 (2010).

Bastin et al., "Salt Selection and Optimisation Procedures for Pharmaceutical New Chemical Entities," Organic Process Research and Development, 4(5):427-435 (2000).

Bishop-Balley et al., "Endothelial Cell Apoptosis Induced by the Peroxisome Proliferator-activated Receptor (PPAR) Ligand 15-Deoxy-Δ-prostaglandin J$_2$,"J. Biol. Chem. 274(24):17042-17048 (1999).

Brockman et al., "Activation of PPARγ Leads to Inhibition of Anchorage-Independent Growth of Human Colorectal Cancer Cells," Gastroenterology 115(5):1049-1055 (1998).

Campbell, I. W., "The Clinical Significance of PPAR Gamma Agonism," Current Molecular Medicine, 5, pp. 349-363 (2005).

Clark et al., "The Nuclear Receptor PPARγ and Immunoregulation: PPARγ Mediates Inhibition of Helper T Cell Responses," J. Immunol. 164(3): 1364-1371 (2000).

Colville-Nash et al., "Inhibition of Inducible Nitric Oxide Synthase by Peroxisome Proliferator-Activated Receptor Agonists: Correlation with Induction of Heme Oxygenase 1," J. Immunol. 161(2):978-984 (1998).

Combs et al., "Inflammatory Mechanisms in Alzheimer's Disease: Inhibition of β-Amyloid-Stimulated Proinflammatory Responses and Neurotoxicity by PPARγ Agonists," J. Neuroscience 20(2):558-567 (2000).

Elstner et al., "Ligands for peroxisome proliferation-activated receptorγ and retinoic acid receptor inhibit growth and induce apoptosis of human breast cancer cells in vitro and in BNX mice," Proc. Natl. Acad. Sci. USA 95(15):8806-8811 (1998).

Gu et al., "Pro12Ala and His447His polymorphisms of PPAR-gamma are associated with polycystic ovary syndrome," Reprod Biomed Online 18(5):644-650 (2009) PMID: 19549442.

Guan et al., "Expression of Peroxisome Proliferator-Activated Receptor γ (PPARγ) in Human Transitional Bladder Cancer and its Role in Inducing Cell Death," Neoplasia (NY) 1(4):330-339 (1999).

Heneka et al., "Peroxisome proliferators-activated receptor gamma agonists protect cerebellar granule cells from cytokine-induced apoptotic cell death by inhibition of inducible nitric oxide synthase," J. Neuroimmunol. 100(1-2):156-168 (1999).

Itoh et al., "Hypertension and Insulin Resistance: Role of Peroxisome Proliferator-Activated Receptor γ," Clin. Exp. Pharmacol. Physiol. 26(7):558-560 (1999).

Jackson et al., "Peroxisome Proliferator-Activated Receptor Activators Target human Endothelial Cells to Inhibit Leukocyte-Endothelial Cell Interaction," Arterioscier. Thromb. Vasc. Biol. 19(9):2094-2104 (1999).

Jain et al., "Ameliorative potential of rosiglitazone in tibial and sural nerve transection-induced painful neuropathy in rats," Pharmacol Res. 59(6):385-392 (2009).

Johnson et al., "Thiazolidinedione Effects on Glucocorticoid Receptor-Mediated Gene Transcription and Differentiation in Osteoblastic Cells," Endocrinology 140(7):3245-3254 (1999).

Kitamura et al., "Increased Expression of Cyclooxygenases and Peroxisome Proliferator-Activated Receptor-γ in Alzheimer's Disease Brains," Biochem. Biophys. Res. Commun. 254(3):582-586 (1999).

Kitamura et al., "Peroxisome Proliferator-activated Receptor γ Induces Growth Arrest and Differentiation Markers of Human Colon Cancer Cells," Jpn. J. Cancer Res. 90(1):75-80 (1999).

Kitamura et al., "Activators of peroxisome proliferators-activated receptor-γ (PPARγ) inhibit inducible nitric oxide synthase expression but increase heme oxygenase-1 expression in rat glial cells," Neurosci. Lett. 262(2):129-132 (1999).

Koika et al., "Association of the Pro12Ala polymorphism in peroxisome proliferator-activated receptor gamma2 with decreased basic metabolic rate in women with polycystic ovary syndrome," Eur J Endrocrinol. 161(2):317-322 (2009).

Komers et al., "Thiazolidinediones—Tools for the Research of Metabolic Syndrome X," Physiol. Res. (Prague) 47(4):215-225 (1998).

Kubota et al., "Ligand for Peroxisome Proliferator-activated Receptor γ (Troglitazone) Has Potent Antitumor Effect against Human Prostate Cancer Both in Vitro and in Vivo," Cancer Res. 58(15):3344-3352 (1998).

Leininger et al., "Peroxisome Proliferator-Activated Receptor γ1 Expression in Porcine White Blood Cells: Dynamic Regulation with Acute Endotoxemia," Biochem. Biophys. Res. Commun. 263(3):749-753 (1999).

Liu et al., "PPARgamma gene C161T substitution is associated with reduced risk of coronary artery disease and decreased proinflammatory cytokine expression," Am Heart J. 154(4):718-24 (2007).

Maeda et al., "Pioglitazone attenuates tactile allodynia and thermal hyperalgesia in mice subjected to peripheral nerve injury," J Pharmacol Sci 108(3):341-347 (2008).

Marx et al., "Macrophages in Human Atheroma Contain PPARγ, Differentiation-Dependent Peroxisomal Proliferation-Activated Receptor γ (PPARγ) Expression and Reduction of MMP-9 Activity through PPARγ Activation in Mononuclear Phagocytes in Vitro," Am. J. Pathol. 153(1):17-23 (1998).

McCarty et al., "Downregulation of Macrophage Activation by PPARγ Suggests a Role for Conjugated Linoleic Acid in Prevention of Alzheimer's Disease and Atherolsclerosis," J. Med. Food 1(3):217-226 (1999).

Mueller et al., "Terminal Differentiation of Human Breast Cancer through PPARγ," Mol. Cell. 1(3):465-470 (1998).

Node et al., "Long-term effects of peroxisome proliferator-activated receptor ligand bezafibrate on N-terminal pro-B type natriuretic peptide in patients with advanced functional capacity impairment," Cardiovasc Diabetol. 28;5:5 (2009).

Ogawa et al., "Association of Bone Mineral Density with a Polymorphism of the Peroxisome Proliferator-Activated Receptor γ Gene: PPARγ Expression in Osteoblasts," Biochem. Biophys. Res. Commun. 260(1):122-126 (1999).

Okazaki et al., "Short-Term Treatment with Troglitazone Decreases Bone Turnover in Patients with Type 2 Diabetes Mellitus," Endocr. J. (Tokyo) 46(6):795-801 (1999).

Okazaki et al., "Thiazolidinediones Inhibit Osteoclast-Like Cell Formation and Bone Resorption in Vitro," Endocrinology 140(11):5060-5065 (1999).

Ricote et al., "The peroxisome proliferation-activated receptorγ (PPARγ) as a regulator of moncyte/macrophage function," J. Leukocyte Biol. 66(5):733-739 (1999).

Rosenfield et al., "Mechanisms of Androgen Induction of Sebocyte Differentiation," Dermatology (Basel) 196(1):43-46 (1998).

San-Millán et al., "The role of genetic variation in peroxisome proliferator-activated receptors in the polycystic ovary syndrome (PCOS): an original case-control study followed by systematic review and meta-analysis of existing evidence," *Clin Endocrinol (Oxf)*. 72(3):383-392 (2010).

Sarafidis et al., "Effect of thiazolidinediones on albuminuria and proteinuria in diabetes: a meta-analysis," *Am J Kidney Dis.* 55(5):835-847 (2010).

Sarraf et al., "Differentiation and reversal of malignant changes in colon cancer through PPARγ," Nat. *Med.* (NY) 4(9):1046-1052 (1998).

Satoh et al., "Thiazolidinediones Suppress Endothelin-1 Secretion from Bovine Vascular Endothelial Cells: A New Possible Role of PPARγ on Vascular Endothelial Function," *Biochem. Biophys. Res. Commun.* 254 (3):757-763 (1999).

Schneider et al., "The proline 12 alanine substitution in the PPARgamma2 gene is associated with increased extent of coronary artery disease in men," *Exp Clin Endocrinol Diabetes* 117(9):519-521 (2009).

Su et al., "A novel therapy for colitis utilizing PPAR-γ ligands to inhibit the epithelial inflammatory response," *J. Clin. Invest.* 104(4):383-389 (1999).

Sugiyama et al., "Peroxisome proliferators-activated receptors are expressed in mouse bone marrow-derived mast cells," *FEBS Lett.* 467(2-3):259-262 (2000).

Tontonoz et al., "Regulation of macrophage gene expression by peroxisome-proliferator-activated receptor gamma: implications for cardiovascular disease," *Curr Opin Lipidol.* 10(6):485-490 (1999).

Unluturk et al., "The Genetic Basis of the Polycystic Ovary Syndrome: A Literature Review Including Discussion of PPAR-gamma," *PPAR Res.* 2007:49109 (2007).

Varmecq et al., "Medical significance of peroxisome proliferators-activated receptors," *Lancet* 354(9173):141-148 (1999).

Yamagishi et al., "Correction of protein kinase C activity and macrophage migration in peripheral nerve by pioglitazone, peroxisome proliferator activated-gamma-ligand, in insulin-deficient diabetic rats," *J Neurochem.* 104(2):491-499 (2008).

Yee et al., "Peroxisome proliferators-activated receptor γ activation in human breast cancer," *Int. J. Oncol.* 15(5):967-973 (1999).

Yu et al., "Peroxisome proliferator-activated receptor-gamma(PPARgamma) agonist improves coronary artery endothelial function in diabetic patients with coronary artery disease," *J Int Med Res.* 38(1):86-94 (2010) PMID: 20233517.

EPO, Supplementary European Search Report dated Feb. 25, 2009 for application No. 04794053.1.

ISA/US, International Search Report dated Apr. 6, 2005 for International application No. PCT/US04/32552.

U.S.P.T.O. Final Office Action, dated Jan. 4, 2006, for U.S. Appl. No. 10/956,251.

EPO—Article 94(3) EPC Communication dated Oct. 27, 2009 for European Patent Application No. EP 04 794 053.1.

EPO—Article 94(3) EPC Communication dated Jun. 14, 2010 for European Patent Application No. EP 04 794 053.1.

EPO—Communication under Rule 71(3) EPC of intent to grant an European patent, dated Jan. 28, 2011 for European Patent Application No. EP 04 794 053.1.

U.S.P.T.O. Non-final Office Action mailed Feb. 23, 2010 for U.S. Appl. No. 12/372,699.

U.S.P.T.O. Final Office Action mailed Jul. 8, 2010 for U.S. Appl. No. 12/372,699.

U.S.P.T.O. Advisory Action mailed Oct. 27, 2010 for U.S. Appl. No. 12/372,699.

U.S.P.T.O. Non-final Office Action mailed Nov. 5, 2010 for U.S. Appl. No. 12/578,498.

Berger, J., et al., "Novel Peroxisome Proliferator-activated Receptor (PPAR) γ and PPARδ Ligands Produce Distinct Biological Effects," *J. Biol. Chem.* 274(10):6718-6725 (1999).

Camacho, I.E., et al., "Peroxisome Proliferator Activated Receptor γ Induces a Clearance Mechanism for the Amyloid β Peptide," *J. Neuroscience* 24(48):10908-10917 (2004).

Campbell, I. W., "The Clinical Significance of PPAR Gamma Agonism," Current Molecular Medicine, 5:349-363 (2005).

Clark, R. W., "The Role of PPARs in Inflammation and Immunity," *J. Leukocyte Biology* 71:388-400 (2002).

Combs, C.K., et al., "Inflammatory Mechanisms in Alzheimer's Disease: Inhibition of Beta Amyloid Stimulated Proinflammatory Responses and Neurotoxicity by PPARγ Agonists," *J. Neuroscience* 20(2):558-567 (2000).

Escribano, L. et al., "Rosiglitazone Rescues Memory Impairment in Alzheimer's Transgenic Mice: Mechanisms Involving a Reduced Amyloid and Tau Pathology," *Neuropsychopharmacology* 35(7):1594-1604 (2010).

Feinstein, D.E., "Therapeutic Potential of Peroxisome Proliferator-Activated Receptor Agonists for Neurological Disease," *Diabetes Technol. Ther.* 5(1):67-73 (2003).

Landreth, G., "Therapeutic Use of Agonists of the Nuclear Receptor PPARγ in Alzheimer's Disease," *Curr. Alzheimer Res.* 4(2):159-164 (2007).

Sastre, M., et al., "Nonsteroidal Anti-Inflammatory Drugs and Peroxisome Proliferator-Activated Receptor-γ Agonists Modulate Immunostimulated Processing of Amyloid Precursor Protein through Regulation of β-Secretase," *J. Neuroscience* 23(30):9796-9804 (2003).

* cited by examiner

101

101

SALTS AND POLYMORPHS OF A POTENT ANTIDIABETIC COMPOUND

1. REFERENCE TO RELATED APPLICATIONS

This application is a continuation application of U.S. patent application Ser. No. 10/956,251, filed Oct. 1, 2004, issued as U.S. Pat. No. 7,223,761, which is entitled to and claims benefit under 35 U.S.C. §119 of U.S. Provisional Application No. 60/508,470, filed Oct. 3, 2003, the contents of which are hereby incorporated by reference in their entireties.

2. FIELD OF THE INVENTION

The present invention relates to salt forms of a potent modulator of the peroxisome proliferator-activated receptor γ ("PPAR γ") receptor and polymorphic forms thereof, compositions comprising the salt forms or polymorphic forms, methods of making the salt forms or polymorphic forms and methods of their use for the diagnosis or treatment of, for example, type II diabetes (and complications thereof), hypercholesterolemia (and related disorders associated with abnormally high or low plasma lipoprotein or triglyceride levels) and inflammatory disorders.

3. BACKGROUND OF THE INVENTION

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. These receptors function as ligand-regulated transcription factors that control the expression of target genes by binding to their responsive DNA sequence as heterodimers with the retinoid X receptor ("RXR"). The target genes encode enzymes involved in lipid metabolism and differentiation of adipocytes. Accordingly, the discovery of transcription factors involved in controlling lipid metabolism has provided insight into regulation of energy homeostasis in vertebrates, and further provided targets for the development of therapeutic agents for disorders such as obesity, diabetes and dyslipidemia.

Peroxisome proliferator-activated receptor γ ("PPARγ") is one member of the nuclear receptor superfamily of ligand-activated transcription factors and has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis and adipocyte differentiation, which has been shown to be a critical step to be targeted for anti-obesity and diabetic conditions.

In view of the clinical importance of PPARγ, compounds that modulate PPARγ function can be used for the development of new therapeutic agents. Potent modulators of PPARγ have been described, for example, in international patent publication no. WO 01/00579 (corresponding to U.S. application Ser. No. 09/606,433), U.S. Patent Publication No. US 2002/0037928 A1 and U.S. Pat. No. 6,200,995 B1 and U.S. Pat. No. 6,583,157 B2. One of these promising modulators, identified herein as compound 101, is in clinical development for diagnosis or therapeutic treatment of type II diabetes. Development of the modulator could yield an oral therapy to treat this illness.

Each pharmaceutical compound has an optimal therapeutic blood concentration and a lethal concentration. The bioavailability of the compound determines the dosage strength in the drug formulation necessary to obtain the ideal blood level. If the drug can crystallize as two or more polymorphs differing in bioavailability, the optimal dose will depend on the polymorph present in the formulation. Some drugs show a narrow margin between therapeutic and lethal concentrations. Chloramphenicol-3-palmitate (CAPP), for example, is a broad-spectrum antibiotic known to crystallize in at least three polymorphic forms and one amorphous form. The most stable form, A, is marketed. The difference in bioactivity between this polymorph and another form, B, is a factor of eight, thus creating the possibility of fatal overdosages of the compound if unwittingly administered as form B due to alterations during processing and/or storage. Therefore, regulatory agencies, such as the United States Food and Drug Administration, have begun to place tight controls on the polymorphic content of the active component in solid dosage forms. In general, for drugs that exist in polymorphic forms, if anything other than the pure, thermodynamically preferred polymorph is to be marketed, the regulatory agency may require batch-by-batch monitoring. Thus, it becomes important for both medical and commercial reasons to produce and market the pure drug in its most thermodynamically stable polymorph, substantially free of other kinetically favored polymorphs.

New forms of such modulators can further the development of formulations for the treatment of illnesses such as type II diabetes. For instance, salt forms of a compound, and polymorphic forms of the salt, are known in the pharmaceutical art to affect, for example, the solubility, dissolution rate, bioavailability, chemical and physical stability, flowability, fractability, and compressibility of the compound as well as the safety and efficacy of drug products based on the compound (see, e.g., Knapman, K. *Modern Drug Discoveries*, 2000: 53).

Accordingly, identification of a salt form or free base of the modulators with optimal physical and chemical properties will advance the development of such PPARγ modulators as pharmaceuticals. The most useful of such physical and chemical properties include: easy and reproducible preparation, crystallinity, non-hygroscopicity, aqueous solubility, stability to visible and ultraviolet light, low rate of degradation under accelerated stability conditions of temperature and humidity, low rate of isomerization of between isomeric forms, and safety for long-term administration to humans.

The free base and certain pharmaceutically acceptable salts of compound 101 are described in U.S. application Ser. No. 09/606,433, corresponding to international patent publication no. WO01/00579, and U.S. Pat. No. 6,583,157 B2. The pharmaceutically acceptable acid salts listed in these patents include, among others, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the salts derived from relatively nontoxic organic acids like acetic, propionic, isobutyric, oxalic, maleic, malonic, benzoic, succinic, suberic, fumaric, mandelic, phthalic, benzenesulfonic, p-toluenesulfonic, citric, tartaric, and methanesulfonic. There is no teaching or suggestion that any of the described salt forms of the above structure are superior to the others.

We have discovered that not all of the salts are equally useful, as judged by the list of properties described above.

Thus, the present invention addresses the need for potent PPARγ modulators and the need for improved solid state forms of PPARγ modulators for manufacturing and bioavailability.

4. SUMMARY OF THE INVENTION

The present invention provides novel salt forms and novel polymorphs of a PPARγ modulator which are useful in the treatment or prevention of conditions and disorders including but not limited to those associated with energy homeostasis, lipid metabolism, adipocyte differentiation, inflammation and diabetic conditions, such as, for example, hyperglycemia and hyperinsulemia. In certain embodiments, the polymorphs are polymorphs of the salts of the invention. The invention also encompasses both hydrous and anhydrous polymorphs of the PPARγ modulator. Without intending to be limited by any particular theory of operation, the storage stability, compressibility, bulk density or dissolution properties of the salts and polymorphs are believed to be beneficial for manufacturing, formulation and bioavailability of the PPARγ modulator. The invention also provides pharmaceutical compositions comprising the salts and/or polymorphs and methods of their use for the treatment of, for example, conditions and disorders associated with energy homeostasis, lipid metabolism, adipocyte differentiation, inflammation and diabetic conditions, including, but not limited to, hyperglycemia and hyperinsulemia.

The salts and polymorphs are formed from compound 101, which is described in U.S. application Ser. No. 09/606,433, corresponding to international patent publication no. WO 01/00579, and in U.S. Pat. No. 6,583,157 B2, the contents of which are hereby incorporated by reference in their entireties. Compound 101 has the following structure (I):

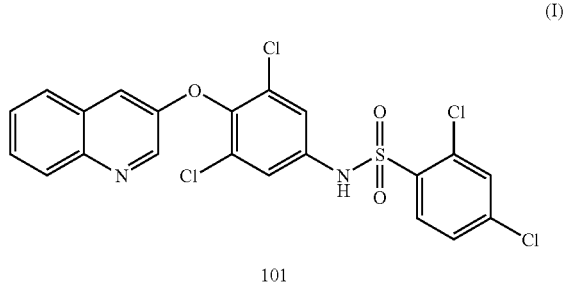

(I)

101

In certain preferred aspects, the present invention provides benzenesulfonic acid salts of compound 101. We have discovered that benzenesulfonic acid salts of compound 101 possess unexpected excellent properties, described in detail below. In further aspects, the present invention provides polymorphs of the benzenesulfonic acid salts of compound 101 identified as Form I and Form II, each described in detail below.

The present invention also provides pharmaceutical compositions comprising a salt form or polymorph of the invention and a pharmaceutically acceptable diluent, excipient or carrier.

The present invention further provides methods for the treatment or prevention of type II diabetes, hypercholesterolemia, inflammatory disorders or a related disorder, comprising administering to a subject in need of such treatment or prevention a therapeutically effective amount of a salt or polymorph of the invention.

The present invention also provides methods for the treatment or prevention of a condition or disorder mediated by the PPARγ receptor, comprising administering to a subject in need of such treatment or prevention a therapeutically effective amount of a salt or polymorph of the invention.

In further embodiments, the present invention provides methods of making, isolating and/or characterizing the salts and polymorphs of the invention.

The novel salt forms and polymorphs of the invention are particularly useful as active pharmaceutical ingredients for the preparation of formulations for use in animals or humans. Thus, the present invention encompasses the use of these solid forms as a final drug product. The salts, polymorphs and final drug products of the invention are useful, for example, for the treatment or prevention of conditions and disorders associated with energy homeostasis, lipid metabolism, adipocyte differentiation and inflammation.

5. BRIEF DESCRIPTION OF THE DRAWINGS

Figure 2:
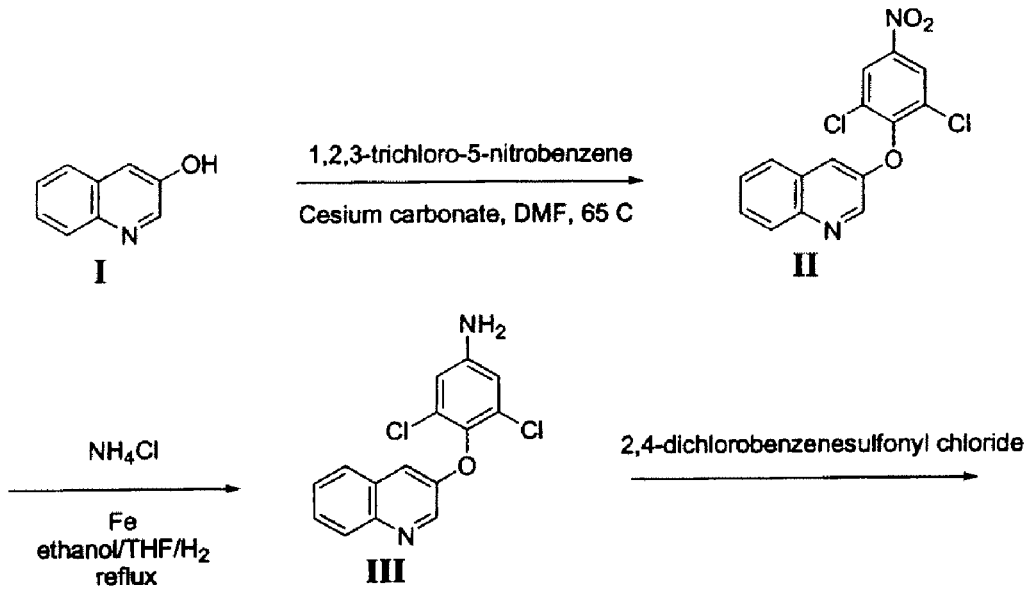
Figure 2:
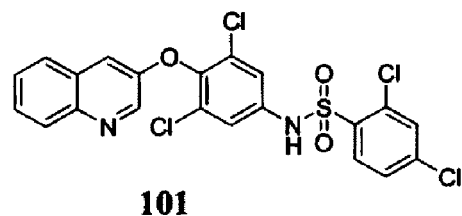
Figure 3:
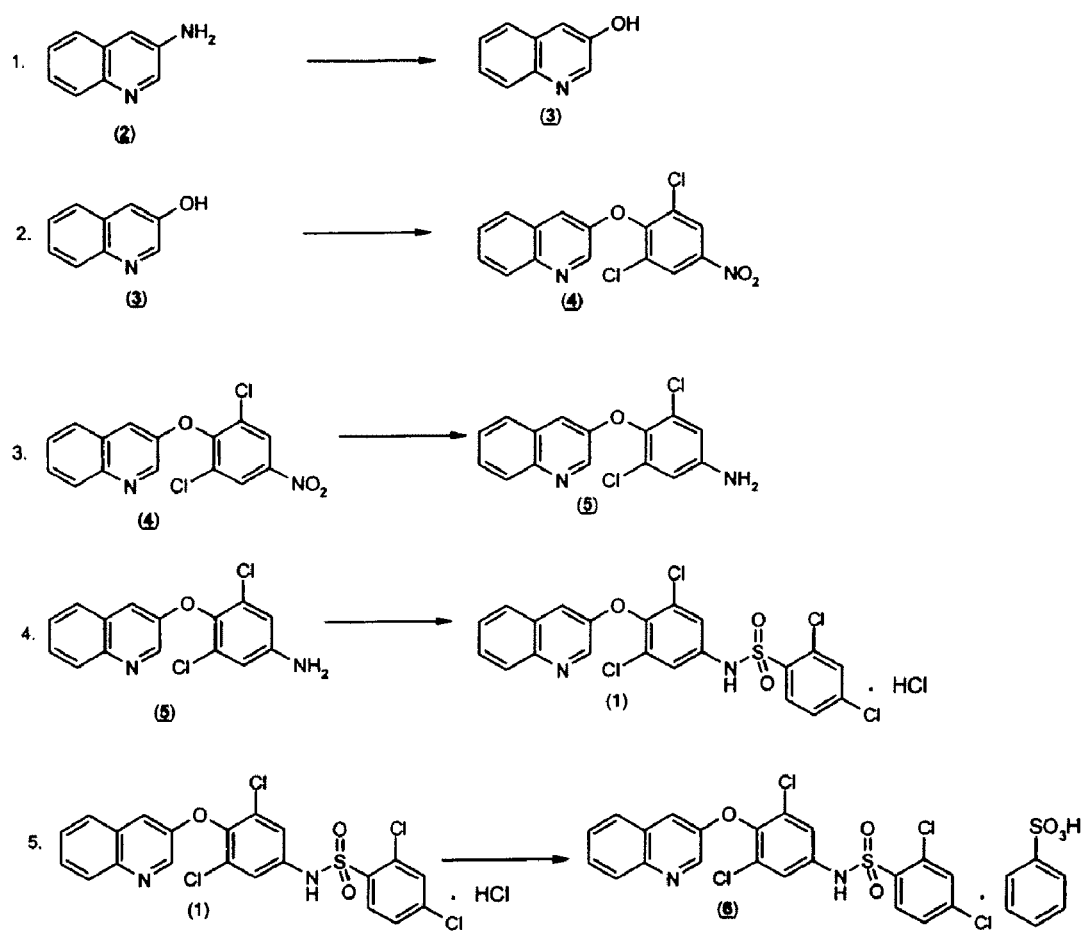
Figure 4:
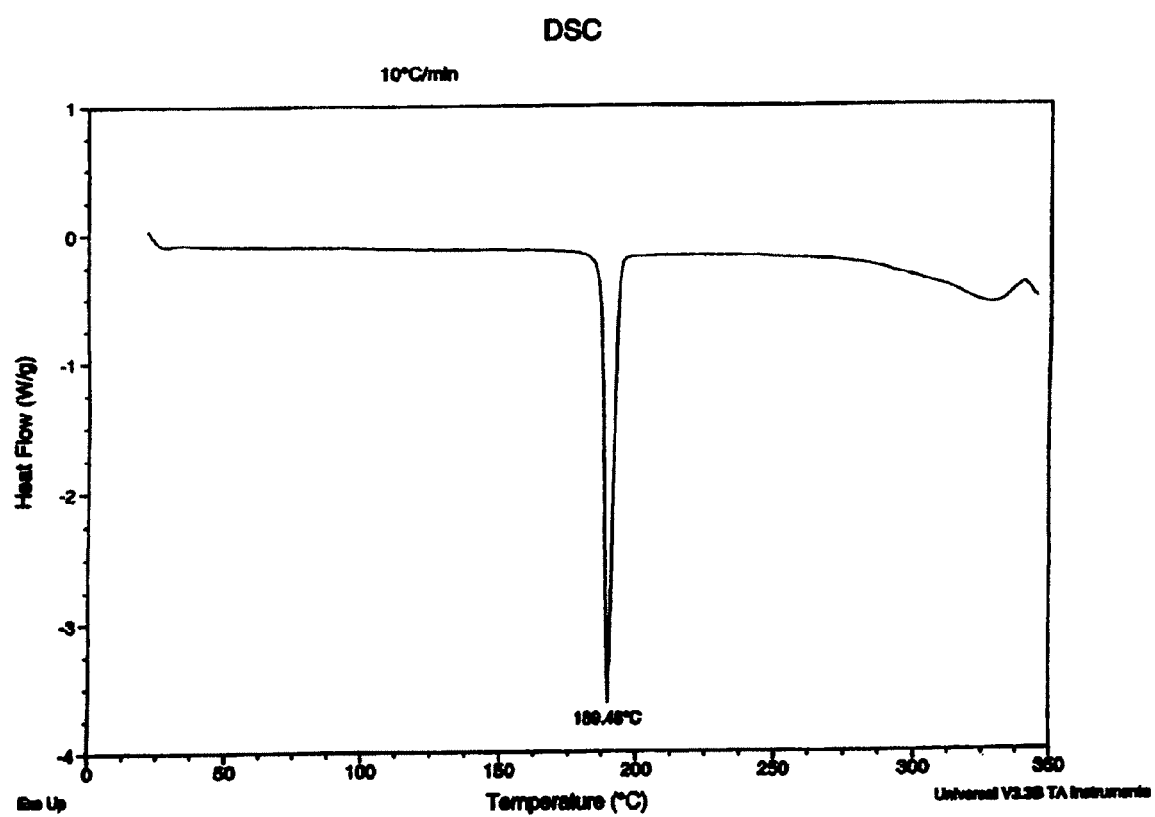
Figure 5:
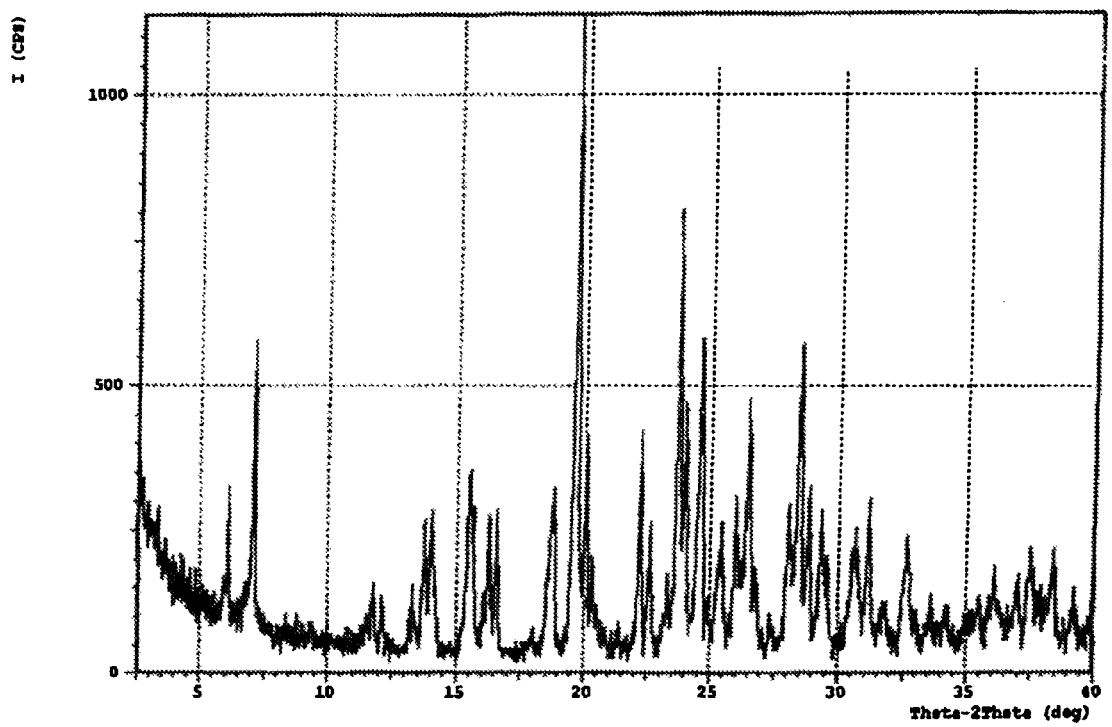
Figure 6:
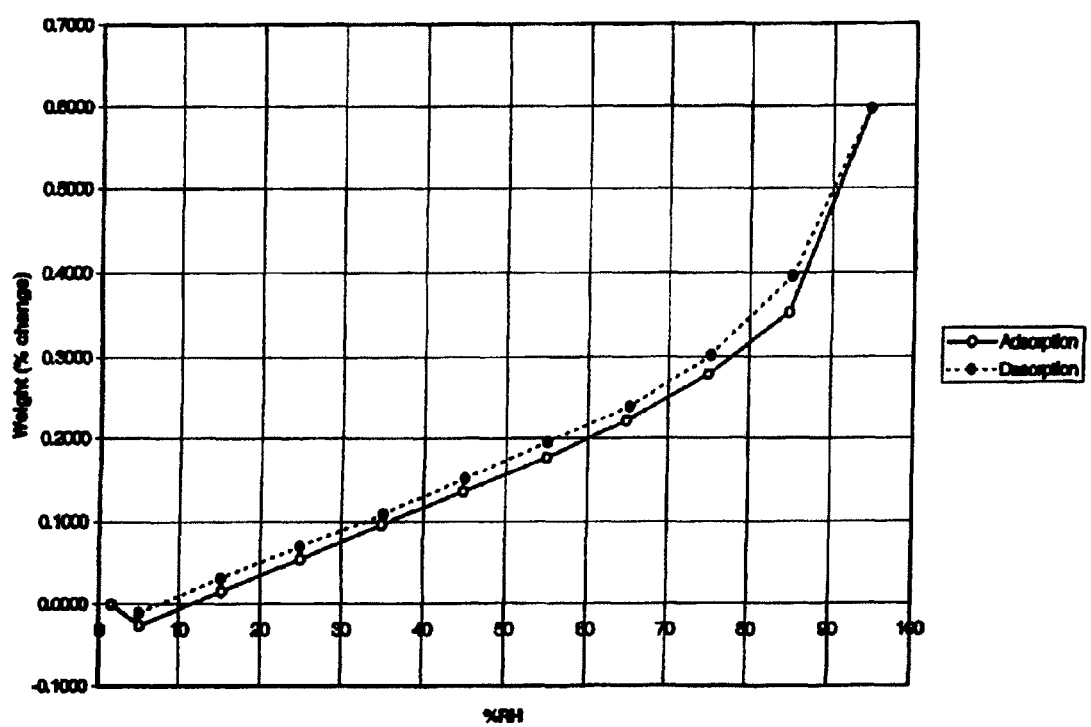
Figure 7:
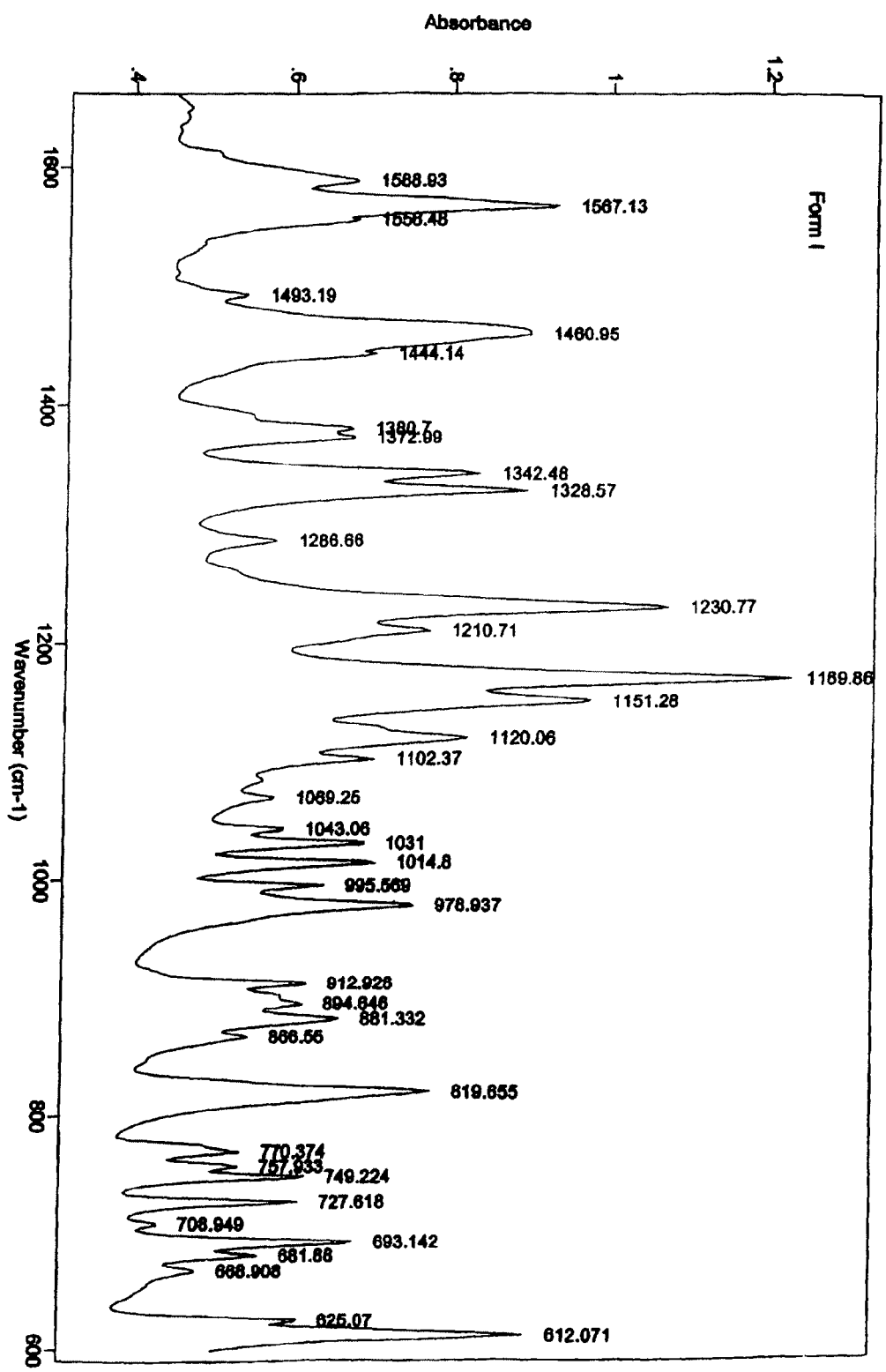
Figure 8:
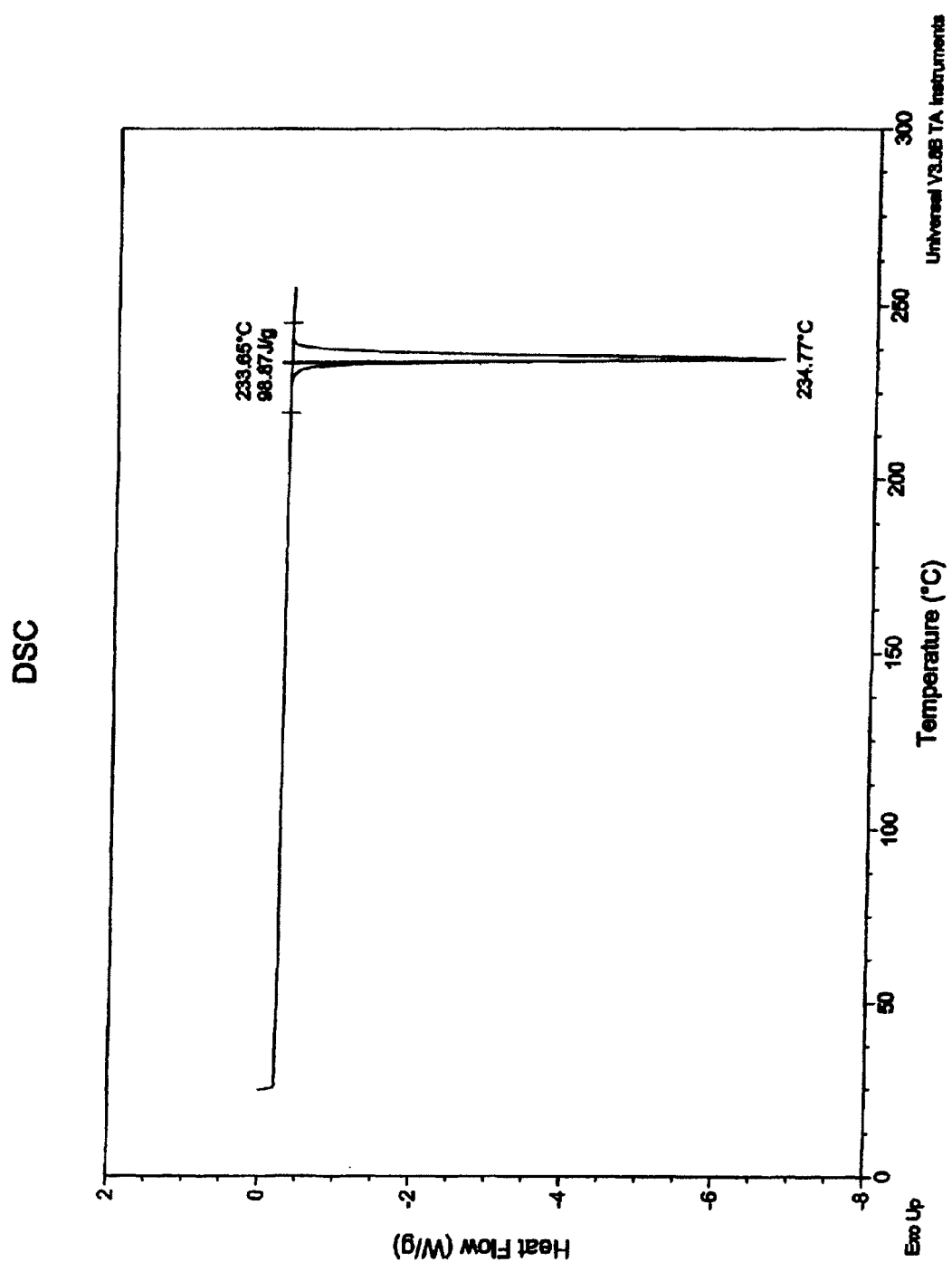
Figure 9:
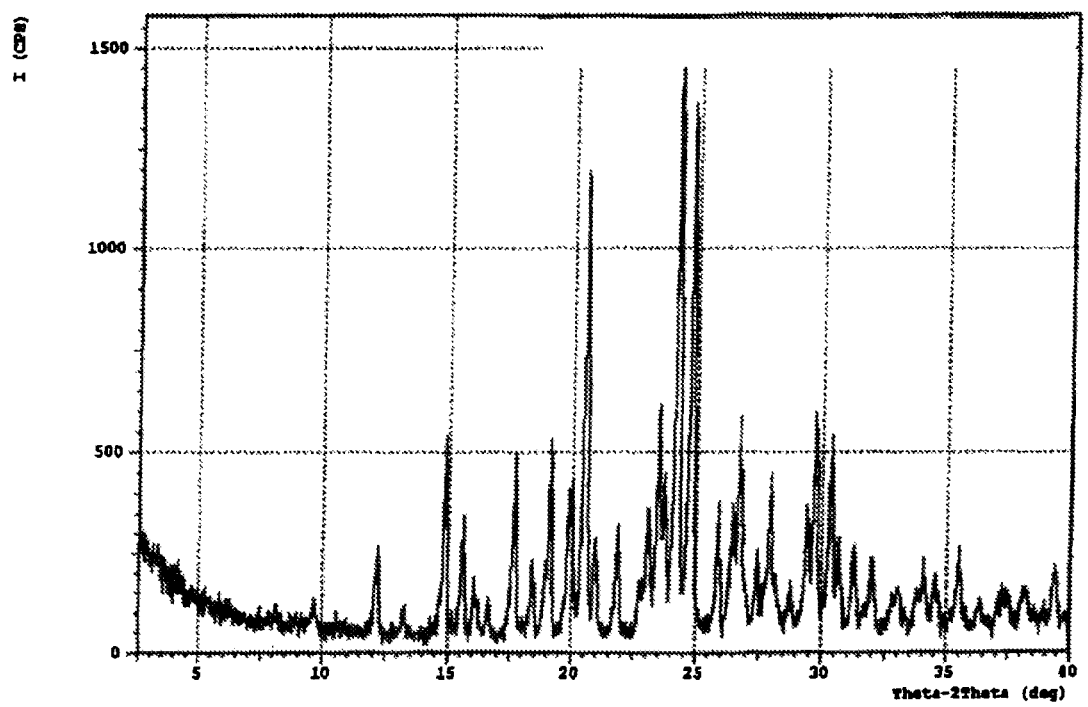
Figure 10:
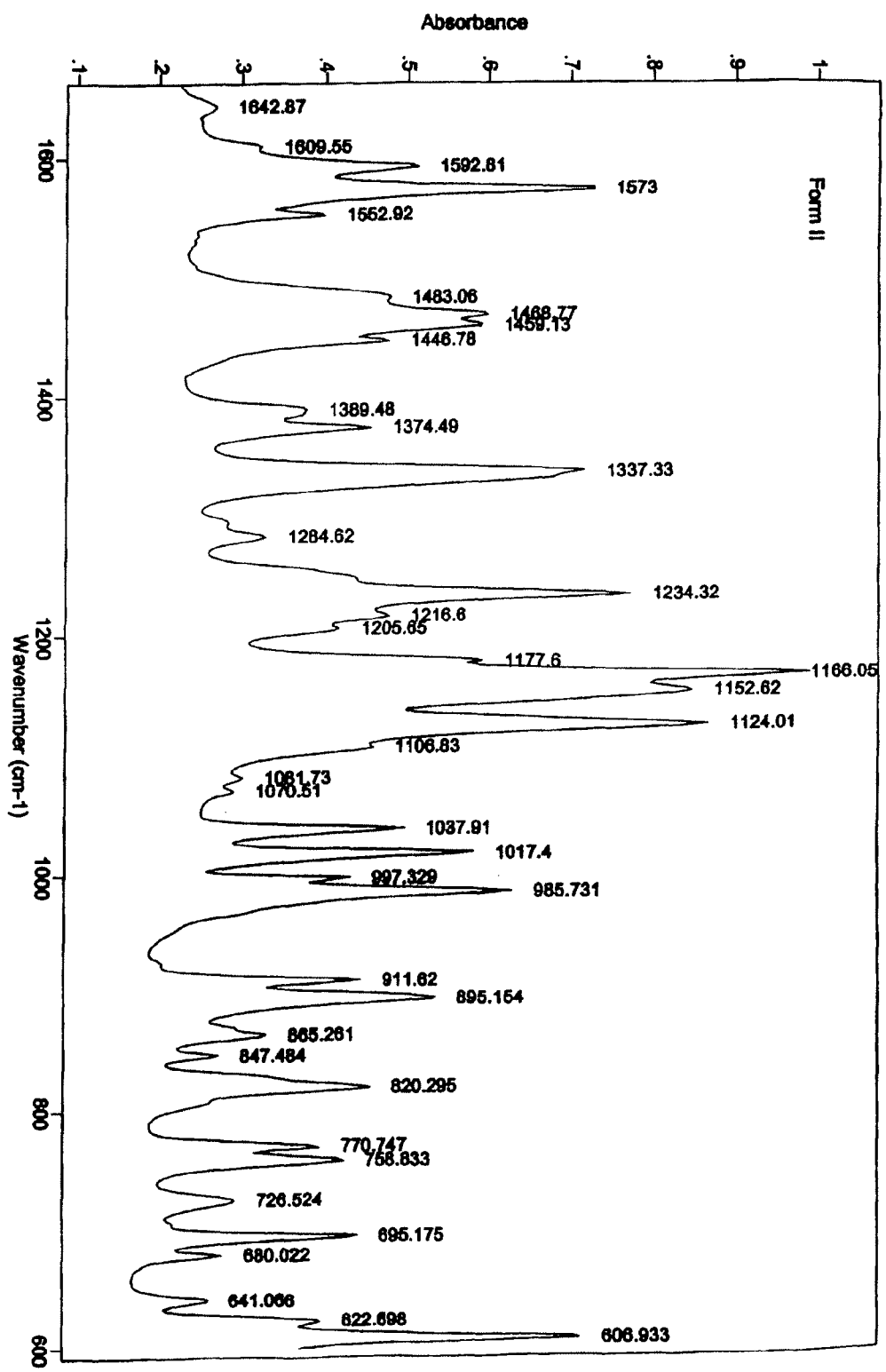

FIG. 1 provides the structure of compound 101;

FIG. 2 provides an exemplary scheme for the synthesis of compound 101;

FIG. 3 provides another exemplary scheme for the synthesis of compound 101;

FIG. 4 provides a differential scanning calorimetry thermogram of a sample comprising Form I;

FIG. 5 provides an X-ray powder diffraction pattern of a sample comprising Form I;

FIG. 6 provides moisture sorption isotherm of a sample comprising Form I;

FIG. 7 provides an infrared spectrum of a sample comprising Form I;

FIG. 8 provides a differential scanning calorimetry thermogram of a sample comprising Form II;

FIG. 9 provides an X-ray powder diffraction pattern of a sample comprising Form I; and FIG. 10 provides an infrared spectrum of a sample comprising Form II.

6. DETAILED DESCRIPTION OF THE INVENTION

6.1 Definitions

The terms "treat", "treating" or "treatment", as used herein, refer to a method of alleviating or abrogating a disease and/or its attendant symptoms. The terms "prevent", "preventing" or "prevention", as used herein, refer to a method of barring a subject from acquiring a disease.

As used herein, "diabetes" refers to type I diabetes mellitus (juvenile diabetes) or type II diabetes mellitus (non-insulin-dependent diabetes mellitus or NIDDM), preferably, type II diabetes mellitus.

As used herein, the term "PPARγ-mediated condition or disorder" or "PPARγ-mediated condition or disease" and the like refers to a condition, disorder, or disease characterized by inappropriate, e.g., less than or greater than normal, PPARγ activity. Inappropriate PPARγ activity might arise as the result of PPARγ expression in cells which normally do not express PPARγ, increased PPARγ expression (leading to, e.g., certain energy homeostasis, lipid metabolism, adipocyte differentiation and inflammatory disorders and diseases), or, decreased PPARγ expression (leading to, e.g., certain energy homeostasis, lipid metabolism, adipocyte differentiation and inflammatory disorders and diseases). A PPARγ mediated condition or disorder may be completely or partially mediated by inappropriate PPARγ activity. However, a PPARγ-mediated condition or disorder is one in which modulation of PPARγ results in some effect on the underlying condition or disease (e.g., a PPARγ modulator results in some improvement in patient well-being in at least some patients). Exemplary PPARγ-mediated conditions and disorders include, but are not limited to, metabolic disorders, e.g., diabetes, type II diabetes, obesity, hyperglycemia, insulin resistance, hyperinsulinemia, hypercholesterolemia, hypertension, hyperlipoproteinemia, hyperlipidemia, hypertriglylceridemia and dyslipidemia, and inflammatory conditions, e.g., rheumatoid arthritis and atherosclerosis.

The term "modulate," in its various forms, refers to the ability of a compound to increase or decrease the function or activity associated with a particular peroxisome proliferator-activated receptor, preferably the PPARγ receptor. Modulation, as described herein, includes the inhibition or activation of PPARγ, either directly or indirectly. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Further, modulation of PPARγ receptor activity is intended to encompass antagonism, agonism, partial antagonism and/or partial agonism of the activity associated with the PPARγ receptor.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The term "therapeutically effective amount" refers to the amount of the subject salt or polymorph that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "alkyl", by itself or as part of another substituent, means, unless otherwise stated, a straight or branched chain, or cyclic hydrocarbon radical, or combination thereof, which may be fully saturated, mono- or polyunsaturated and can include di- and multi-valent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$. Also included in the term "heteroalkyl" are those radicals described in more detail below as "heteroalkylene" and "heterocycloalkyl."

In certain embodiments an aryl group is "substituted." In these embodiments, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from the group consisting of hydrogen, ($C_1$-$C_8$)alkyl and heteroalkyl, unsubstituted aryl, (unsubstituted aryl)-($C_1$-$C_4$)alkyl, and (unsubstituted aryl)oxy-($C_1$-$C_4$)alkyl.

The term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)).

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Particular salts described below include "besylate salts" or "benzenesulfonate salts" of compound 101 of the invention. A besylate or benzenesulfonate salt is an acid addition salt formed from benzenesulfonic acid.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g., IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term, "amorphous form," as used herein, refers to a noncrystalline form of a substance.

In addition to salt forms and polymorphs, the invention provides compounds which are in a prodrug form. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include petidyl derivatives of a compound.

The compound of the present invention may also contain unnatural proportions of atomic isotopes at one or more of the atoms. For example, the compound may be radiolabeled with radioactive isotopes, such as for example tritium ($^3H$), iodine-125 ($^{125}I$) sulfur-35 ($^{35}S$), or carbon-14 ($^{14}C$). Radiolabled compounds are useful as therapeutic agents, e.g., cancer therapeutic agents, research reagents, e.g., binding assay reagents, and diagnostic agents, e.g., in vivo imaging agents. All isotopic variations of the compound of the present invention, whether radioactive or not, are intended to be encompassed within the scope of the present invention.

6.2 Embodiments of the Invention

The present invention is directed to salt forms and polymorphs of compound 101, compositions comprising the salts and polymorphs alone or in combination with other active ingredients, methods of their use in the modulation of receptor activity, particularly PPARγ activity. While not intending to be bound by any particular theory of operation, the storage stability, compressibility, density or dissolution properties of the salts and polymorphs are beneficial for manufacturing, formulation and bio-availability of the PPARγ modulator.

Preferred salts and polymorphs of the invention are those that are characterized by physical properties, e.g., stability, solubility and dissolution rate, appropriate for clinical and therapeutic dosage forms. Preferred polymorphs of the invention are those that are characterized by physical properties, e.g., crystal morphology, compressibility and hardness, suitable for manufacture of a solid dosage form. Such properties can be determined using techniques such as X-ray diffraction, microscopy, IR spectroscopy and thermal analysis, as described herein and known in the art.

The salts and polymorphs of the invention are useful in the treatment or prevention of conditions and disorders associated with diabetic conditions, energy homeostasis, lipid metabolism, adipocyte differentiation and inflammation (see, Ricote et al., Nature 391:79-82 (1998) and Jiang et al., Nature 391:82-86 (1998)). For example, salts and polymorphs of the invention are useful in the treatment of metabolic disorders, such as type II diabetes. Additionally, the compounds of the invention are useful for the prevention and treatment of complications of metabolic disorders, such as type II diabetes, e.g., neuropathy, retinopathy, glomerulosclerosis and cardiovascular disorders.

6.2.1 Salts of Compound 101

In one aspect, the present invention provides particular pharmaceutically acceptable salts of compound 101, a potent modulator of the PPARγ receptor, having particular utility for the treatment or prevention of conditions and disorders associated with energy homeostasis, lipid metabolism, adipocyte differentiation, inflammation, and diabetes or diabetic conditions. This aspect of the invention provides HCl, HBr, tosylate and besylate salts of compound 101.

In preferred embodiments, the present invention provides besylate salts of compound 101. As shown above, compound 101 has the general formula (I):

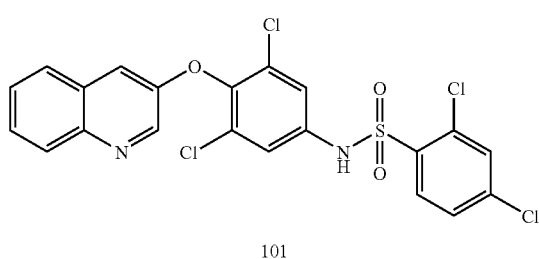

(I)

101

In the benzenesulfonate salt forms of compound 101, the benzenesulfonic acid is according to formula (II):

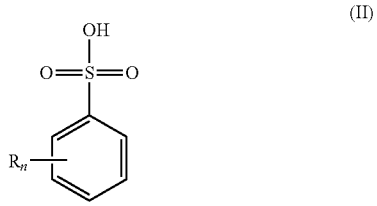

(II)

In formula (II), the phenyl ring is optionally substituted with R which can be any aryl substituent described above, and n is any integer from 1 to 5. In certain embodiments, R is heteroalkyl, alkyl or hydrogen, and n is any integer from 1 to 5. In further embodiments, R can be alkyl or hydrogen, and n is any integer from 1 to 5. In some embodiments, R is lower alkyl or hydrogen, and n is any integer from 1 to 5. In particular embodiments, each R is hydrogen. The preferred besylate salt of compound 101 is provided by formula (III):

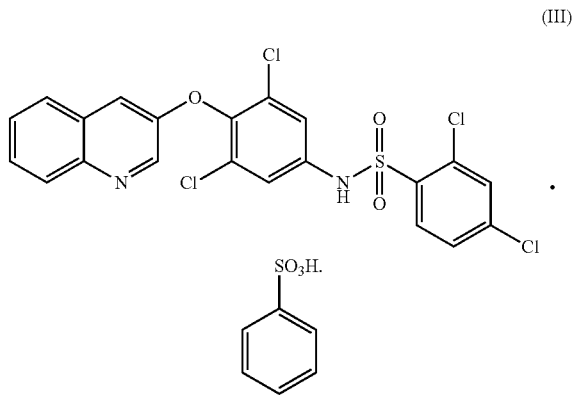

(III)

Each salt of the invention can be made from a preparation of compound 101 (see FIG. 1). Compound 101 can be synthesized or obtained according to any method apparent to those of skill in the art. In preferred embodiments, compound 101 is prepared according to the methods described in detail in the examples below, in U.S. Pat. No. 6,583,157 and in international patent publication WO 01/00579, the contents of which are hereby incorporated by reference in their entireties.

Alternatively, compound 101 can be prepared by isolating a salt of compound 101 as described below and converting such a salt of compound 101 to the neutral form by treatment with an appropriate base. For example, compound 101 can be prepared by isolating the hydrochloride salt of compound 101 by filtration, then converting it to the neutral form by treatment with monobasic sodium carbonate in ethyl acetate, or other suitable base. In such embodiments, the hydrochloride salt of compound 101 can be prepared by any method known to one of skill in the art. For example, the hydrochloride salt of compound 101 can be prepared by reacting 3,5-dichloro-4-(quinolin-3-yloxy)-phenylamine with 2,4-dichlorobenzenesulfonylchloride and hydrochloric acid to yield 2,4-dichloro-N-[3,5-dichloro-4-quinolin-3-yloxy)phenyl]-benzenesulfonamide HCl as described in Example 7.

Exemplary schemes for the synthesis of compound 101 from 3-hydroxyquinoline are provided in FIGS. 2 and 3 and are described in detail in the examples below. Compound 101 prepared by any method can be contacted with an appropriate acid, either neat or in a suitable inert solvent, to yield the salt forms of the invention. For example, compound 101 can be contacted with an appropriate benzenesulfonic acid to yield the besylate salt forms of the invention.

As shown in detail in the examples below, the besylate salt of compound 101, and polymorphs thereof, display surprisingly superior stability and hygroscopic properties when compared to other salts of compound 101.

6.2.2 Polymorphs

The present invention also provides polymorphs of compound 101, a potent modulator of the PPARγ receptor, having particular utility for the treatment or prevention of conditions and disorders associated with energy homeostasis, lipid metabolism, adipocyte differentiation and inflammation. In certain embodiments, the polymorphs of the invention are polymorphs of the besylate salt of compound 101 described above. Compound 101 and its preparation are described above and in the examples below.

Each polymorph of the invention can be made from a preparation of compound 101 (see FIG. 1). Solid compound 101 can be dissolved and then crystallized from the solvent mixtures described below to yield the polymorphic forms of the invention. In particular embodiments of the invention, a besylate salt of compound 101 can be dissolved and then crystallized from the solvent mixtures described below to yield the polymorphic forms of the invention.

In one embodiment, the present invention provides Form I of a besylate salt of compound 101 (2,4-Dichloro-N-[3,5-dichloro-4-(quinolin-3-yloxy)-phenyl]-benzenesulfonamide benzenesulfonate salt). In one embodiment, the Form I polymorph of the besylate salt of compound 101 has a melting point of about 180° C. or greater. In a particular embodiment, the Form I polymorph has a melting point between about 180 and 200° C. When an exemplary Form I polymorph was examined by differential scanning calorimetry according to the methods described in the examples below, it had an endotherm at between about 186.3° C. and about 189.5° C. and an enthalpy of fusion of between about 81.5 J/g and about 89.9 J/g. In further embodiments, the Form I polymorph of the besylate salt of compound 101 has an X-ray powder diffraction pattern similar to that of FIG. 5 using Cu Kα radiation. For example, particular Form I polymorphs of the invention have major X-ray powder diffraction pattern peaks at 7.0, 19.5, 22.0, 24.0, 24.5 and 28° 2θ using Cu Kα radiation. In certain embodiments, the Form I polymorph of the invention has major X-ray powder diffraction pattern peaks at one, two, three, four, five or six of the X-ray powder diffraction pattern peaks at 7.0, 19.5, 22.0, 24.0, 24.5 and 28° 2θ using Cu Kα radiation. In further embodiments, the Form I polymorph of the invention has both a melting point between about 186 and 200° C. and major X-ray powder diffraction pattern peaks at one, two, three, four, five or six of the X-ray powder diffraction pattern peaks at 7.0, 19.5, 22.0, 24.0, 24.5 and 28° 2θ using Cu Kα radiation. In still further embodiments, the Form I polymorph of the invention has major infrared absorbance peaks at one, two, three, four, or five of the infrared absorbance peaks at 1567, 1461, 913, 895, and 881 cm$^{-1}$.

Form I of the besylate salt of compound 101 can be made by any method of making Form I apparent to those of skill in the art based upon the teachings herein. In certain embodiments, Form I can be crystallized from ethanol solutions of compound 101 and a hydrate of benzenesulfonic acid. Preferably, an ethanol solution of benzenesulfonic acid hydrate (Aldrich) can be added to solid compound 101 under heat to complete solution; cooling the solution yields Form I. Form I can also be crystallized from solutions of ethyl acetate and ethanol as described in the examples below.

In another embodiment, the present invention provides Form II of the besylate salt of compound 101 (2,4-Dichloro-N-[3,5-dichloro-4-(quinolin-3-yloxy)-phenyl]-benzenesulfonamide benzenesulfonate salt). In one embodiment, the Form II polymorph of the besylate salt of compound 101 has a melting point of about 230° C. or greater. In a particular embodiment, the Form II polymorph has a melting point between about 230 and 240° C. An exemplary Form II of the besylate salt of compound 101 displayed surprising stability and had a melting temperature of about 233° C. When an exemplary Form II polymorph was examined by differential scanning calorimetry according to the methods in the examples below, it had an endotherm at about 233.7° C. and an enthalpy of fusion of about 98.9 J/g. In further embodiments, the Form II polymorph of the besylate salt of compound 101 has an X-ray powder diffraction pattern similar to that of FIG. 9 using Cu Kα radiation. For example, particular Form II polymorphs of the invention have major X-ray powder diffraction pattern peaks at 15, 19, 20.5, 23.5, 24.5, 25, 26.5, 29.5 and 30.5° 2θ using Cu Kα radiation. In certain embodiments, the Form II polymorph of the invention has major X-ray powder diffraction pattern peaks at one, two, three, four, five, six, seven or eight of the X-ray powder diffraction pattern peaks at 15, 19, 20.5, 23.5, 24.5, 25, 26.5, 29.5 and 30.5° 2θ using Cu Kα radiation. In certain embodiments, the Form II polymorph of the invention has both a melting point between about 230 and 240° C. and major X-ray powder diffraction pattern peaks at one, two, three, four, five, six, seven or eight of the X-ray powder diffraction pattern peaks at 15, 19, 20.5, 23.5, 24.5, 25, 26.5, 29.5 and 30.5° 2θ using Cu Kα radiation. In further embodiments, the Form II polymorph of the invention has major infrared absorbance peaks at one, two, three, four, or five of the infrared absorbance peaks at 1573, 1469, 1459, 912, and 859 cm$^{-1}$.

Form II of the besylate salt of compound 101 can be made by any method apparent to those of skill in the art to make Form II based upon the teachings herein. In certain embodiments, Form II can be crystallized from solutions of ethyl acetate and ethanol as described in the examples below. Preferably, Form H of the besylate salt of compound 101 can be prepared by adding an ethanol solution of benzenesulfonic acid to solid compound 101 under heat. The reaction suspension can be stirred under heat, then cooled under further stirring, which yields Form II of the besylate salt of compound 101.

In certain embodiments, the present invention also contemplates obtaining Form I or II of a besylate salt of compound 101 by crystallization of either of Forms I or II of the besylate salt of compound 101 and conversion of the crystallized form to the other form (e.g., crystallization of Form I and conversion of Form I to Form II) in solution or in the solid state.

As shown in detail in the examples below, the besylate salt of compound 101 exhibits superior properties to other acid addition salts of compound 101. The Form I and Form II polymorphs of the besylate salt of compound 101, and polymorphs thereof, display advantageous stability and hygroscopicity for use in a formulation for administration to animals or humans. Form II of the besylate salt of compound 101 is preferred over Form I of the besylate salt of compound 101 because of its greater stability.

6.2.3 Compositions

In another aspect, the present invention provides pharmaceutical compositions for modulating PPARγ activity in humans and animals. The compositions comprise a salt or polymorph of the present invention and a pharmaceutically acceptable diluent, excipient or carrier. In certain embodiments, a pharmaceutical composition of the invention comprises a pure salt or polymorph of compound 101. For example a pharmaceutical composition of the invention can comprise pure Form I or pure Form II.

As used herein, a salt or polymorph that is "pure", i.e., substantially free of other polymorphs, contains less than about 10% of one or more other polymorphs, preferably less than about 5% of one or more other polymorphs, more preferably less than about 3% of one or more other polymorphs, most preferably less than about 1% of one or more other polymorphs.

The pharmaceutical compositions for the administration of the salts or polymorphs of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the salt or polymorph is included in an amount sufficient to produce the desired effect upon the process, condition or disease to be modulated, prevented, or treated.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups, solutions, or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452, and 4,265,874 to form osmotic therapeutic tablets for controled release.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The salts or polymorphs of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

For topical use, creams, ointments, jellies, solutions or suspensions, etc., containing the salts or polymorphs of the present invention are employed. As used herein, topical application is also meant to include the use of mouth washes and gargles.

The pharmaceutical composition and method of the present invention may further comprise other therapeutically active compounds as noted herein which are usually applied in the treatment or prevention of the above mentioned pathological conditions.

6.2.4 Methods of Use

In yet another aspect, the present invention provides methods of treating PPARγ-mediated conditions or diseases by administering to a subject having such a disease or condition, a therapeutically effective amount of a salt or polymorph or composition of the invention. The subject can be an animal such as, for example, a mammal, including, but not limited to, a primate (e.g., a human), a cow, a sheep, a goat, a horse, a dog, a cat, a rabbit, a rat, a mouse and the like.

Depending on the biological environment (e.g., cell type, pathological condition of the host, etc.), these compounds can activate or block the actions of PPARγ. By activating, i.e., agonizing, the PPARγ receptor, the compounds will find use as therapeutic agents capable of modulating conditions mediated by the PPARγ receptor. As noted above, examples of such conditions include type II diabetes. Thus, PPARγ receptor agonists can be used to treat conditions including type II diabetes. Additionally, the compounds are useful for the prevention and treatment of complications of diabetes (e.g., neuropathy, retinopathy, glomerulosclerosis, and cardiovascular disorders), and preventing or treating hyperlipidelinia. Still further, the compounds are useful for the modulation of inflammatory conditions which most recently have been found to be controlled by PPARγ (see, Ricote et al, Nature 391:79-82 (1998) and Jiang et al., Nature 391:82-86 (1998)). Examples of inflammatory conditions include rheumatoid arthritis and atherosclerosis. Compounds that act via antagonism of PPARγ are useful for treating obesity, hypertension, hyperlipidemia, hypercholesterolemia, hyperlipoproteinemia, and metabolic disorders.

In therapeutic use for the treatment of obesity, diabetes, inflammatory conditions or other conditions or disorders mediated by PPARγ, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Depending on the disease to be treated and the subject's condition, the polymorphs of the present invention may be administered by oral, parenteral (e.g., intramuscular, intraperitoneal, intravenous, ICV, intracisternal injection or infusion, subcutaneous injection, or implant), inhalation spray, nasal, vaginal, rectal, sublingual, or topical routes of administration and may be formulated, alone or together, in suitable dosage unit formulations containing conventional non-toxic pharmaceutically acceptable diluents, excipients or carriers appropriate for each route of administration.

In the treatment or prevention of conditions which require PPAR$\gamma$ receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The polymorphs may be administered on a regimen of 1 to 4 times per day, preferably once or twice per day.

It will be understood, however, that the specific dose level and frequency of dosage for any particular patient may be varied and will depend upon a variety of factors including the activity of the specific polymorph employed, the metabolic stability and length of action of that polymorph, the age, body weight, general health, sex, diet, mode and time of administration, rate of excretion, drug combination, the severity of the particular condition, and the host undergoing therapy.

The salts and polymorphs of the present invention can be combined with other compounds having related utilities to treat or prevent metabolic disorders and inflammatory conditions, complications thereof and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-diabetic agents, can be used in dosages which are less than the expected amounts when used alone, or less than the calculated amounts for combination therapy.

For example, suitable agents for combination therapy include those that are currently commercially available and those that are in development or will be developed. Exemplary agents useful in the treatment of metabolic disorders include, but are not limited to: (a) anti-diabetic agents such as insulin, sulfonylureas (e.g., meglinatide, tolbutamide, chlorpropamide, acetohexamide, tolazamide, glyburide, glipizide and glimepiride), biguanides, e.g., metformin (Glucophage®), $\alpha$-glucosidase inhibitors (acarbose), thiazolidinone compounds, e.g., rosiglitazone (Avandia®, troglitazone (Rezulin®) and pioglitazone (Actos®); (b) $\beta_3$ adrenergic receptor agonists, leptin or derivatives thereof and neuropeptide Y antagonists; (c) bile acid sequestrants (e.g., cholestyramine and colestipol), HMG-CoA reductase inhibitors, e.g., statins (e.g., lovastatin, atorvastatin, fluvastatin, pravastatin and simvastatin), nicotinic acid (niacin), fibric acid derivatives (e.g., gemfibrozil and clofibrate) and nitroglycerin. Exemplary agents useful in the treatment of inflammatory conditions include, but are not limited to: (a) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (b) cyclooxygenase-2 (COX-2) inhibitors such as celecoxib (Celebrex®) and rofecoxib (Vioxx®) and (c) inhibitors of phosphodiesterase type IV (PDE-IV). The weight ratio of the polymorph of the present invention to the second active ingredient may be varied and will depend upon the effective dose of each ingredient. Generally, an effective dose of each will be used. Thus, for example, when a polymorph of the present invention is combined with an NSAID the weight ratio of the polymorph of the present invention to the NSAID will generally range from about 1000:1 to about 1:1000, preferably about 200:1 to about 1:200. Combinations of a salt or polymorph of the present invention and other active ingredients will generally also be within the aforementioned range, but in each case, an effective dose of each active ingredient should be used.

In certain embodiments, the salts and polymorphs of the invention may be used to treat or prevent a variety of other indications. Such indications include, but are not limited to, metabolic conditions such as diabetes (including type I and type II diabetes), hypertension, angina pectoris, dyslipidemia (including hypertriglyceridemia, hyperlipoproteinemia, and hypercholesterolemia), gout, nephropathy and other renal diseases secondary to diabetes, diabetic neuropathy, other insulin-resistance-related diseases, polycystic ovarian syndrome, glucocorticoid-induced insulin resistance, obesity, bone disorders, female-specific conditions (including excessive climacteric uterine bleeding), and acne; neurological disorders such as Alzheimer's disease, neuroinflammation, ischemic stroke, closed-head injury, and multiple sclerosis; proliferative disorders such as atherosclerosis, restenosis, colon cancer, prostate cancer, breast cancer, liposarcoma, epithelial cell cancers, uroepithelial cancer, and other cancers; and inflammatory or immune disorders such as rheumatoid arthritis, inflammatory bowel disease, colitis, Crohn's disease, macular degeneration, other inflammatory disorders, and other immune disorders. Rationales suggesting the utility of the salts and polymorphs of the present invention for treating or preventing such indications are discussed below.

PPARγ modulators are believed useful to treat obesity because PPARγ agonists promote adipocyte differentiation and fat accumulation. PPARγ modulators also block normal hormone-mediated differentiation of preadipocytes into adipocytes. (See Wright et al., J. Biol. Chem. 275(3):1873-1877 (2000).) PPARγ agonists can inhibit expression of ob gene (leptin production) in mature adipocytes. It therefore follows that PPARγ modulators will increase leptin production with ensuing decrease in appetite and food consumption. (See Sinha et al., Metab. Clin. Exp., 48(6):786-791 (1999).). Further, hyperleptinemia conditions induced with a PPARγ modulator in rats result in downregulation of PPARγ expression and upregulation of fatty acid-oxidizing enzymes. These effects are accompanied by a reversal of adipocyte differentiation.

Moreover, PPARγ agonists upregulate UCP2 expression in adipocytes and skeletal muscle, resulting in increased energy expenditure. (See Viguerie-Bascands et al., Biochem. Biophys. Res. Commun. 256(1):138-141 (1999) and Camirand et al., Endocrinology 139(1):428-431 (1998).) PPARγ is critical for controlling expression of UCP2 and UCP3 in adipose tissue. (See Kelly et al., Endocrinology 139(12):4920-4927 (1998).) Taken together, these results suggest that relatively short-term treatment with high dose of PPARγ modulator will have long-lasting effects on obesity; conventional treatments of obesity reduce fat content in mature adipocytes but leaves them with lipogenic enzymes capable of rapid resynthesis of fat. Such rapid resynthesis is likely to be responsible for treatment failure. (See Zhou et al., Proc. Natl. Acad. Sci. USA 96(5):2391-2395 (1999).)

PPARγ modulators are believed useful for treatment of hypertension because PPARγ agonists suppress endothelin-1 secretion by vascular endothelial cells and result in decreased blood pressure. (See Satoh et al., Biochem. Biophys. Res. Commun. 254 (3):757-763 (1999) and Itoh et al., Clin. Exp. Pharmacol. Physiol. 26(7):558-560 (1999).) PPARγ agonists also decrease blood pressure in various models of hypertension. (See Komers et al., Physiol. Res. (Prague) 47(4):215-225 (1998).)

PPARγ modulators are believed useful for treatment of lipid disorders because PPARγ has been implicated in systemic glucose and lipid homeostasis. (See Kliewer et al., Curr. Opin. Genet. Dev. 8(5):576-581 (1998).) PPARγ agonists also improve hypertriglyceridemia. (See Berger et al., J. Biol. Chem. 274(10):6718-6725 (1999).) Further, PPARγ agonists are antihyperlipidemic. (See Henke et al., J. Med. Chem. 41(25):5020-5036 (1998).) Finally, a PPARγ activator has been shown to increase high-density lipoprotein (HDL) in a dose-dependent manner and to decrease VLDL, LDL and triglycerides. (See Bisgaier et al., J. Lipid Res. 39(1):17-30 (1998).)

PPARγ modulators are believed useful for treatment of atherosclerosis because activated monocytes/macrophages express PPARγ and PPARγ activation downregulates the induced macrophage production of IL-1 and TNFα. This implies a potential role for PPARγ in atherosclerosis. (See McCarty et al., J. Med. Food 1 (3):217-226 (1999).) In addition, PPARγ mediates the effects of non-esterified fatty acids (NEFA) on smooth muscle cells, which alter the extracellular matrix in the intima of small and large arteries. These changes can lead to increased deposition of LDL and may be associated with the etiology of atherosclerosis. Modulators of PPARγ can affect this process. (See Olsson et al., Diabetes 48(3):616-622 (1999).)

Further, PPARγ agonists inhibit proliferation, hypertrophy and migration of vascular smooth muscle cells induced by growth factors. These processes are crucial in the development of vascular remodeling and atherosclerosis. PPARγ is involved in negative regulation of monocyte/macrophage function in atherosclerotic plaques and regulates expression of matrix metalloprotease-9, an enzyme implicated in plaque rupture. In this case, a PPARγ agonist may be useful. (See Marx et al., Am. J. Pathol. 153(1):17-23 (1998) and Shu et al., Biochem. Biophys. Res. Commun. 267(1):345-349 (2000).) PPARγ is expressed in macrophage foam cells of human sclerotic lesions. (See Ricote et al., Proc. Natl. Acad. Sci. USA 95(13):7614-7619 (1998).) PPARγ is also expressed in atherosclerotic plaques and in endothelial cells. In endothelial cells, PPARγ agonists markedly attenuate the TNFα-induced expression of VCAM-1 and ICAM-1 (vascular cell adhesion molecules) in vitro. PPARγ agonists significantly reduce monocyte/macrophage homing to atherosclerotic plaques in apoE-deficient mice. These effects combined may have beneficial effects in modulating inflammatory response in atherosclerosis. (See Pasceri et al., Circulation 101(3):235-238 (2000).)

Finally, human genetic evidence also suggests that PPARγ plays a significant role in atherogenesis, independent from effects on obesity and lipid metabolism, possibly via a direct local vascular wall effect. (See Wang et al., Cardiovasc. Res. 44(3):588-594 (1999).) In the past year, there has been a significant increase in research implicating PPARγ in macrophage biology, cell cycle regulation and atherosclerosis, particularly as a regulator of monocyte/macrophage function. (See Ricote et al., J. Leukocyte Biol. 66(5):733-739 (1999).)

PPARγ modulators are believed useful for treatment of bone disorders because TZDs inhibit in vitro bone nodule formation and mineralization. (See Johnson et al., Endocrinology 140(7):3245-3254 (1999).) PPARγ polymorphism affects bone mineral density in postmenopausal women. (See Ogawa et al., Biochem. Biophys. Res. Commun. 260(1):122-126 (1999).) TZDs are potent inhibitors of bone resorption in vitro. Thus, TZDs may suppress bone resorption in diabetic patients and prevent bone loss. (See Okazaki et al., Endocrinology 140(11):5060-5065 (1999).) Short-term treatment of diabetic patients with TZD decreases bone turnover. This effect is noted before significant improvement on glucose metabolism, suggesting that effect operates directly on bone. Dual effects on glucose and bone metabolism may lead to spared bone mass in diabetic patients. (See Okazaki et al., Endocr. J. (Tokyo) 46(6):795-801 (1999).)

PPARγ modulators are believed useful for treatment of female-specific conditions because PPARγ agonists can be used to inhibit excessive climacteric uterine bleeding in women. (See Urban et al., WO 98/39006.)

PPARγ modulators are believed useful for treatment of acne because PPARγ is implicated in the differentiation of sebocytes. PPARγ agonists may be used in the treatment of acne, other skin disorders associated with differentiation of epidermal cells, or other proliferative diseases of the skin. (See Rosenfield et al., Dermatology (Basel) 196(1):43-46 (1998); Rivier et al., FR 2773075 A1; and Pershadsingh et al., U.S. Pat. No. 5,981,586.)

PPARγ modulators are believed useful for treatment of disorders relating to cellular proliferation because in combination with a retinoid-X receptor agonist, a PPARγ agonist reduces uncontrolled cell proliferation, including cancer, restenosis and atherosclerosis. PPARγ agonists, either alone or in combination with known agents, may reduce proliferative response seen following angioplasty, vessel transplant or endarectomy.

PPARγ modulators are believed useful for treatment of Alzheimer's Disease because PPARγ agonists inhibit b-amyloid stimulated secretion of proinflammatory products by microglia and monocytes that are responsible for neurotoxicity and astrocyte activation. They also arrest differentiation of monocytes into activated macrophages, and inhibit b amyloid-stimulated expression of IL-6, TNFα and cyclooxygenase-2. (See Combs et al., J. Neuroscience 20(2):558-567 (2000).) In temporal cortex from patients diagnosed with Alzheimer's Disease, cyclooxygenase-1, cyclooxygenase-2, and PPARγ levels were increased. Certain agents that activate PPARγ inhibit COX-2 expression in glial cells. (See Kitamura et al., Biochem. Biophys. Res. Commun. 254(3):582-586 (1999).) In addition, PPARγ agonists protect cerebellar granule cells from cytokine-induced apoptotic death by inhibition of iNOS. (See Heneka et al., J. Neuroimmunol. 100(1-2):156-168 (1999).) Finally, activated monocytes/macrophages express PPARγ and PPARγ activation downregulates induced macrophage production of IL-1 and TNFα This process is potentially implicated in Alzheimer's Disease. (See McCarty et al., J. Med. Food 1(3):217-226 (1999).)

PPARγ modulators are believed useful for treatment of neuroinflammation because PPARγ agonists inhibit LPS and IFN-g induced expression of iNOS by glial cells. (See Kitamura et al., Neurosci. Lett. 262(2):129-132 (1999).) Also, PPARγ ligands may be relevant for other disorders associated with neuroinflammation, such as ischemic stroke, closed-head injury, and multiple sclerosis.

PPARγ modulators are believed useful for treatment of certain cancers because anti-angiogenic effect of PPARγ agonists are mediated by apoptotic stimulus on endothelial cells. (See Bishop-Balley et al., J. Biol. Chem. 274(24):17042-17048 (1999).) Also, PPARγ agonists induce terminal differentiation and growth arrest of human colon cancer cells. (See Kitamura et al., Jpn. J. Cancer Res. 90(1):75-80 (1999) and Sarraf et al., Nat. Med. (NY) 4(9):1046-1052 (1998).) PPARγ agonists also enhance the anti-proliferative effects of retinoic acid on human colon cancer cells. (See Brockman et al., Gastroenterology 115(5):1049-1055 (1998).) In addition, a particular PPARγ agonist has potent anti-tumor effects against human prostate cancer in vitro and in vivo. (See Kubota et al., Cancer Res. 58(15):3344-3352 (1998).)

PPARγ agonists can also inhibit proliferation of cultured human breast tumor cells and induce apoptosis. Effects are also seen in vivo in mice. (See Elstner et al., Proc. Natl. Acad. Sci. USA 95(15):8806-8811 (1998).) PPARγ agonists can induce terminal differentiation of malignant breast epithelial cells. (See Mueller et al., Mol. Cell. 1(3):465-470 (1998) and Yee et al., Int. J. Oncol. 15(5):967-973 (1999).) PPARγ agonists are useful in the treatment of liposarcomas. (See Evans et al., WO 98/29120.) PPARγ is highly expressed in all human transitional epithelial cell cancers, including uroepithelial human cancers. PPARγ agonists induce differentiation and inhibit proliferation. (See Guan et al., Neoplasia (NY) 1(4): 330-339 (1999).) Finally, differentiation of many cell types (hepatocytes, fibroblasts, adipocytes, keratinocytes, myocytes, and monocyte/macrophages) involves PPARγ. Therefore, PPAR-γ modulators may play a role in treating malignancies that result from these and other cell types. (See Varmecq et al., Lancet 354(9173):141-148 (1999).)

PPARγ modulators are believed useful for treatment of inflammatory or immune disorders because PPARγ is markedly upregulated in activated macrophages. PPARγ is implicated in negative regulation of monocyte/macrophage function, including generation of inflammatory cytokines and expression of iNOS, gelatinase B and scavenger receptor A. Therefore, PPARγ agonists may be of value. (See Marx et al., Am. J. Pathol. 153(1):17-23 (1998).) Incremental therapeutic benefit of NSAIDs (some of which activate PPARγ) in the treatment of rheumatoid arthritis may be mediated via PPARγ activation. (See Jiang et al., Nature 391(6662):82-86 (1998).) PPARγ agonists inhibit iNOS production by activated macrophages. PPARγ agonists may accordingly be useful. (See Colville-Nash et al., J. Immunol. 161(2):978-984 (1998).)

In addition, PPARγ agonists attenuate antigen-induced cytokine production by bone-marrow-derived mast cells. (See Sugiyama et al., FEBS Lett. 467(2-3):259-262 (2000).) Recently, an immunomodulatory role for PPARγ has been described in cells critical to the innate immune system, including monocytes and macrophages. PPARγ agonists mediate significant inhibition of proliferative responses of helper T-cell clones and freshly isolated splenocytes. Thus, IL-2 production by the T-cell clones is inhibited by PPARγ agonists, which accordingly may have utility as immunosuppressants. (See Clark et al., J. Immunol. 164(3): 1364-1371 (2000).) PPARγ is also implicated as a regulator of monocyte/macrophage function. (See Ricote et al., J. Leukocyte Biol. 66(5):733-739 (1999).) PPARγ expression in white blood cells may play a role in host response to acute inflammatory challenge and may prove to be an important target for anti-inflammatory control. (See Leininger et al., Biochem. Biophys. Res. Commun. 263(3):749-753 (1999).)

Moreover, PPARγ activators may help limit chronic inflammation mediated by vascular cell adhesion molecule VCAM-1 and monocytes. (See Jackson et al., Arterioscier. Thromb. Vasc. Biol. 19(9):2094-2104 (1999).) PPARγ agonists also markedly reduce colonic inflammation in a mouse model of inflammatory bowel disease (IBD). PPARγ agonists may be useful in treating colitis and Crohn's disease. (See Su et al., J. Clin. Invest. 104(4):383-389 (1999).)

Finally, PPARγ modulators are believed useful for treatment of optical disorders such as macular generation because the anti-angiogenic affect of PPARγ agonists is mediated by apoptotic stimulus on endothelial cells. This suggests that such agonists may be useful in the treatment of macular degeneration. (See Bishop-Balley et al., J. Biol. Chem. 274 (24):17042-17048 (1999).)

In particularly preferred embodiments, the present methods are directed to the treatment or prevention of type II diabetes using a salt or polymorph of the invention either alone or in combination with a second therapeutic agent selected from anti-diabetic agents such as insulin, sulfonylureas (e.g., meglinatide, tolbutamide, chlorpropamide, acetohexamide, tolazamide, glyburide, glipizide and glimepiride), biguanides, e.g., metformin (Glucophage®), α-glucosidase inhibitors (acarbose), thiazolidinone compounds, e.g., rosiglitazone (Avandia®, troglitazone (Rezuling) and pioglitazone (Actos®). When used in combination, the practitioner can administer a combination of the therapeutic agents, or administration can be sequential.

7. EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electrospray ionization (ESI) mass spectrometry analysis was conducted on a Hewlett-Packard 1100 MSD electrospray mass spectrometer using the HP 1100 HPLC for sample delivery.

Mass spectrometry results are reported as the ratio of mass over charge. The compound was dissolved in methanol at 0.1 mg/mL and 1 microliter was infused with the delivery solvent into the mass spectrometer, which scanned from 100 to 1500 daltons. The compound could be analyzed in the positive ESI mode, using 1:1 acetonitrile/water with 1% acetic acid as the delivery solvent. The compound could also be analyzed in the negative ESI mode, using 2 mM NH$_4$OAc in acetonitrile/water as delivery solvent.

X-ray powder diffraction analysis was performed using a Shimadzu XRD-6000 X-ray powder diffractometer using Cu Kα radiation. The instrument's fine focus X-ray tube voltage and amperage were set to 40 kV and 40 mA, respectively. The divergence and scattering slits were set at 1°, and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed to check the instrument alignment. Data were collected and analyzed using XRD-6000 v.4.1

In certain experiments, differential scanning calorimetry was performed using a TA instruments differential scanning calorimeter 2920 calibrated with an indium standard. Samples were placed in aluminum sample pans and covered. Samples were equilibrated at 25° C. and heated under a nitrogen purge at a controlled rate of 10° C./min up to a final temperature of 350° C.

In other experiments, differential scanning calorimetry was performed using a TA instruments Q100 differential scanning calorimeter. Samples were placed in aluminum sample pans and covered. Samples were equilibrated at 25° C. and heated under a nitrogen purge at a controlled rate of 10° C./min up to a final temperature of 250° C.

Moisture sorption/desorption data were collected on a VTI SGA-100 Vapor Sorption Analyzer. Sorption and desorption data were collected over a range of 5% to 95% relative humidity ("RH") at 10% RH intervals under nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Scanning electron microscopy (SEM) was performed using an FEI Quanta 200 scanning electron microscope. A large field detector was used under low vacuum mode. The pole piece of the instrument was equipped with an electron secondary detector cone. Beam voltage ranged from 4.7-5.0 kB, and the chamber pressure ranged from 69.3 to 118.7 Pa. Image resolution was 1024×948. Samples were prepared for analysis by placing a small amount on carbon tape mounted on an aluminum stub. The instrument was calibrated for magnification using NIST standards. Data was collected using xTm, build number 1564 and analyzed using XT Docu (v. 3.2). Magnification reported on SEM images was calculated upon initial data acquisition.

The solid-state infrared (IR) spectra were obtained using a Perkin-Elmer 1600 infrared spectrometer. The compound was dispersed at approximately 1% in a KBr pellet.

7.1 Example 1

Synthesis of Compound 101

This example provides an exemplary synthesis of compound 101. Alternate methods of synthesizing compound 101, including methods of synthesizing acid addition salts of compound 101 are described below; still other alternate synthetic methods will be apparent to those of skill in the art.

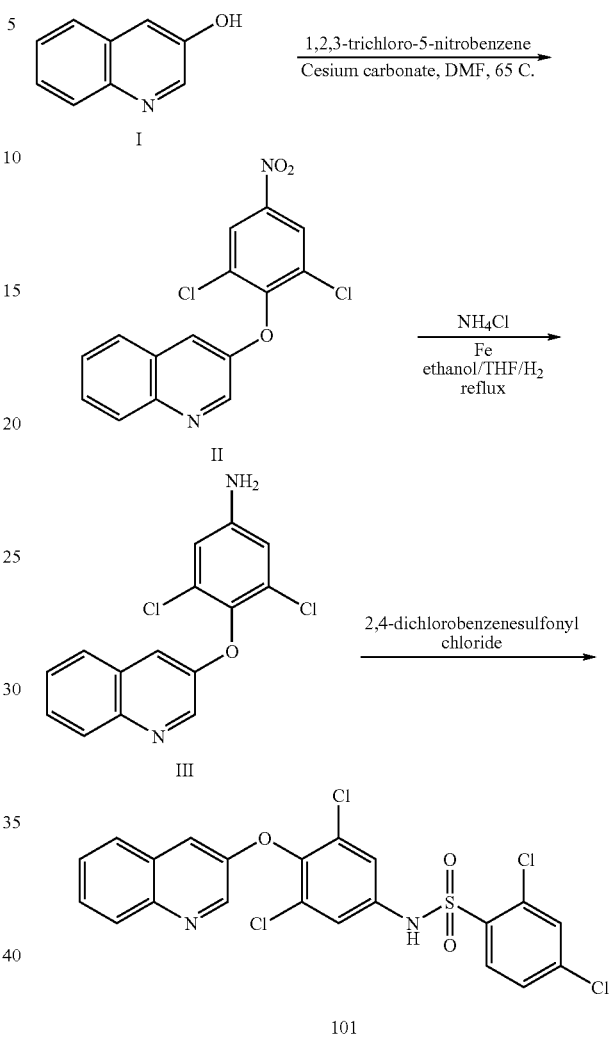

3-(2,6-Dichloro-4-nitro-phenoxy)3,4-dihydro-quinoline (II)

3-Hydroxyquinoline (1) (prepared according to the procedure of Naumann et. al., Synthesis 4:279-281 (1990)) (3 g) and 1,2,3-trichloro-5-nitrobenzene (4.7 g) were dissolved in DMF (80 mL) and heated with cesium carbonate (7.4 g) for 2 h at 60° C. The reaction was poured into ice/water (500 mL). The resulting off-white precipitate was collected by filtration and rinsed with hexane to afford compound II as a solid (6.9 g) suitable for use in the next reaction.

$^1$H NMR in CDCl$_3$ δ 8.863 (d, J=2.2 Hz, 1H), 8.360 (s, 2H), 8.106 (d, J=8.6 Hz, 1H), 7.646 (m, 2H), 7.529 (d, J=8.6 Hz, 1H), 7.160 (d, J=2.2 Hz, 1H).

3,5-Dichloro-4-(3,4-dihydro-quinolin-3-yloxy)-phenylamine (III)

To a solution of compound II (6.9 g) in ethanol/THF/water (ratio 40:20:10) was added ammonium chloride (3.3 g) and powdered iron (3.4 g). This mixture was heated to reflux for 5 h. The hot mixture was then filtered through Celite and concentrated. The residue was dissolved in ethyl acetate and washed with saturated $NaHCO_3$ solution followed by water and then brine. The solution was dried over magnesium sulfate and concentrated to afford compound III as an off-white solid (5.6 g).

$^1$H NMR in (DMSO) δ8.846 (d, J=2.9 Hz, 1H), 8.010 (m, 1H), 7.915 (m, 1H), 7.645 (m, 1H), 7.560 (m, 1H), 7.401 (d, J=2.9 Hz, 1H), 6.778 (s, 2H), 5.762 (s, 2H).

2,4-Dichloro-N-[3,5-dichloro-4-(quinolin-3-yloxy)-phenyl]-benzenesulfonamide (101)

Treatment of the aniline III with 2,4-dichlorobenzenesulfonyl chloride according to conventional methods gave compound 101

$^1$H NMR ($d_6$-acetone) δ 9.9 (1H, br s), 8.794 (1H, d, J=2.9 Hz), 8.23 (11H, d, J=8.4 Hz), 8.035 (1H, br d, J=8.4 Hz), 7.793 (1H, d, J=1.5 Hz), 7.78 (1H, m), 7.62-7.70 (2H, m), 7.57 (1H, td, J=6.8, 1.2 Hz), 7.476 (2H, s), 7.364 (1H, d, J=2.6 Hz). MS (M−H) 511.0.

7.2 Example 2

PPARγ Ligand Binding

Using methods similar to Lehmann et al., J. Biol. Chem. 270:12953-12956 (1995), compound 101, prepared according to Example 1, exhibited an $IC_{50}$ of less than 1 μM in a PPARγ ligand binding assay utilizing [$^3$H]-BRL 49653 as the radioligand.

7.3 Example 3

Crystallization of an HCL Salt of Compound 101

Compound 101 was recrystallized as an HCl salt. Compound 101 prepared according to Example 1, except that an $SnCl_2$ reduction was used for reduction of compound II to compound III, was suspended in ~3.5 L warm ethanol. About 240 ml 21% NaOEt in ethanol was added to form a complete solution. A solution of 145 ml of concentrated HCl (~3 eq) in 450 ml of ethanol was added to the warm solution and allowed to slow cool to room temperature. The solid precipitate was collected by vacuum filtration. The product was slurried in water (2 L) and recollected by filtration. After air drying, the product was dried under vacuum at 70° C. to constant weight of 311 g. The anyhydrous HCl salt of compound 101 was confirmed by NMR and CHN.

HCl salts of compound 101 formed small rhomboid crystals or needles. SEM showed plates or prismatic particles. DSC showed varying endothermal events of, for instance, 125.2, 161.5, 222.6, 190.3, 224.9, 235.6, 242.4 and 182° C.; endothermic events were broad, and enthalpies of fusion could not be calculated. XRPD showed crystalline or partially crystalline particles.

7.4 Example 4

Crystallization of an HBR Salt of Compound 101

Compound 101 was recrystallized as an HBr salt. A solution of 0.98 g 48% HBr (3 eq) in ethanol (3 ml) was added to a solution of the free base form of compound 101 (1 g) in ethanol (20 mL). For this example, compound 101 was prepared according to Example 1, except that an $SnCl_2$ reduction was used for reduction of compound II to compound III. The resulting clear solution was placed in an ultrasonic bath until a white precipitate formed. After standing at room temperature for 10 minutes, the suspension was heated to reform a clear solution. This solution was allowed to cool slowly in a jacketed flask overnight. Solids (0.829 g) were collected by vacuum filtration and dried to constant weight under vacuum. The HBr salt of compound 101 was confirmed by NMR and CHN.

HBr salts of compound 101 formed crystals, and SEM showed plates. DSC showed endothermal events of 255.4 and 261.7° C. from a single sample, and an enthalpy of fusion of 158.5 J/g. One or both endothermal events could have been due to sample melting. XRPD showed crystalline or partially crystalline particles.

7.5 Example 5

Crystallization of a Tosylate Salt of Compound 101

Compound 101 was recrystallized as a tosylate salt. A solution of p-toluenesulphonic acid monohydrate (4.5 g, 2 eq) in ethanol (55 ml)/water (11 ml) was added to a solution of the free base form of compound 101 (6 g) in ethanol (120 ml). For this example, compound 101 was prepared according to Example 1, except that an $SnCl_2$ reduction was used for reduction of compound II to compound III. The mixture was heated to form a clear solution. After cooling to room temperature, some solvent was removed under a stream of nitrogen until a white precipitate became apparent. Rewarming the suspension formed a clear solution which was allowed to stir with slow cooling for 60 hrs. The solids were collected by vacuum filtration and dried to constant weight under vacuum to obtain 6.4 g solid with a melting point of 215-220° C. These were resuspened in ethanol (30 ml) and heated to dissolve. After slow cooling the solid was collected and dried under vacuum to give 6.19 g solid with a melting point of 218-220° C. The tosylate salt of compound 101 was confirmed by NMR.

Tosylate salts of compound 101 formed crystals, and SEM showed irregular particles. DSC showed an endothermal event of 220.6° C. and an enthalpy of fusion of 86.76 J/g. XRPD showed crystalline or partially crystalline particles.

7.6 Example 6

Crystallization of form I of a Besylate salt of Compound 101

This example provides an example of a small-scale crystallization of Form I the besylate salt of compound 101 from the free base of compound 101. Compound 101 was recrystallized as Form I with benzenesulfonic acid ($PhSO_3H$-$xH_2O$; Aldrich). 3.9 g benzenesulfonic acid was dissolved in 5 ml ethanol, and this ethanol solution was added to 5.02 g solid free base compound 101. For this example, compound 101 was prepared according to Example 1, except that an $SnCl_2$ reduction was used for reduction of compound II to compound III. The mixture was rinsed with 5 ml ethanol, and additional ethanol was further added to a total of 25 ml. The mixture was heated to form a complete solution and then slowly cooled with stirring. Solid Form I, 5.57 g, was collected by filtration and rinsed with ethanol.

Synthesis of Salts of Compound 101 according to Examples 7 and 8

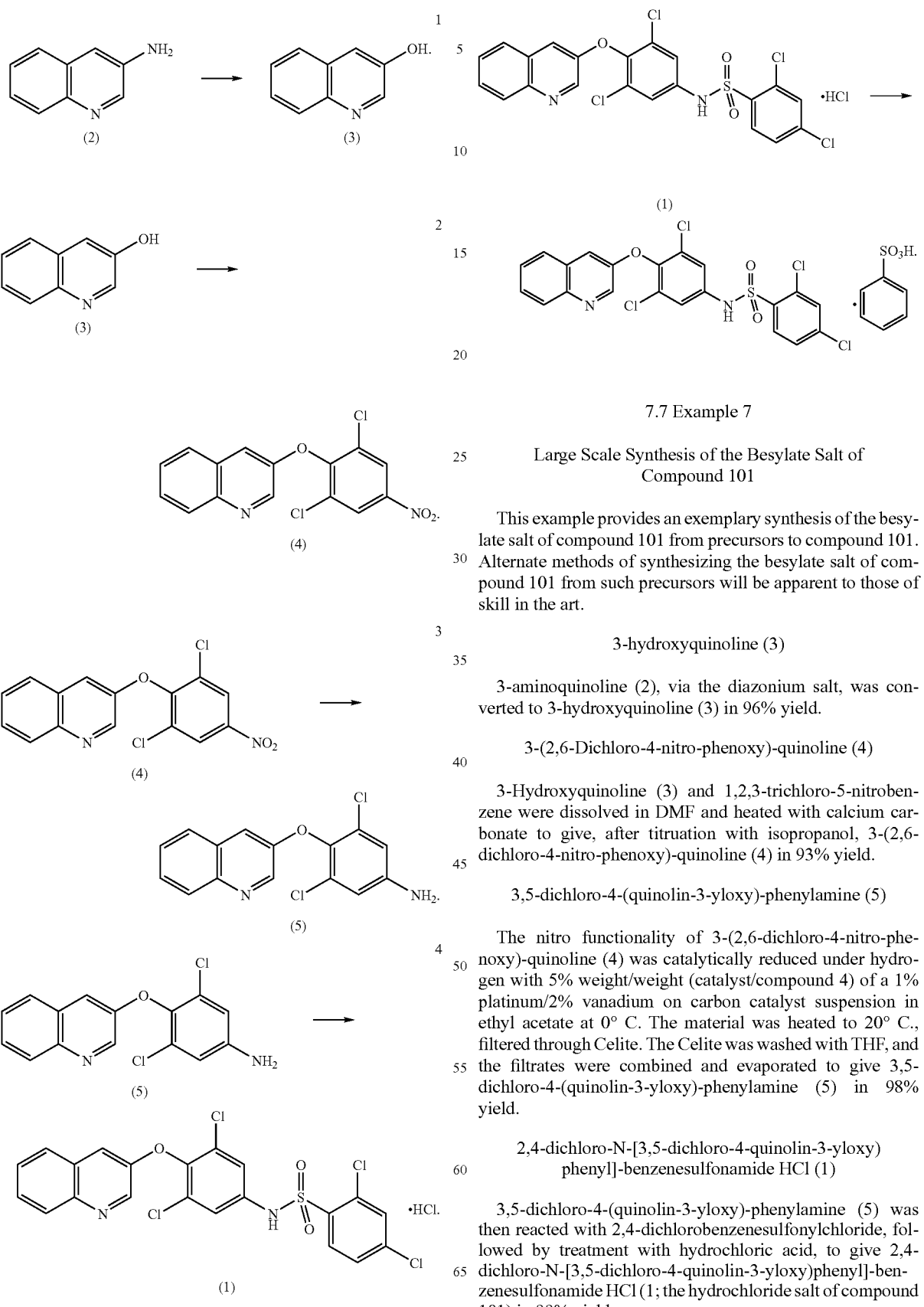

7.7 Example 7

Large Scale Synthesis of the Besylate Salt of Compound 101

This example provides an exemplary synthesis of the besylate salt of compound 101 from precursors to compound 101. Alternate methods of synthesizing the besylate salt of compound 101 from such precursors will be apparent to those of skill in the art.

3-hydroxyquinoline (3)

3-aminoquinoline (2), via the diazonium salt, was converted to 3-hydroxyquinoline (3) in 96% yield.

3-(2,6-Dichloro-4-nitro-phenoxy)-quinoline (4)

3-Hydroxyquinoline (3) and 1,2,3-trichloro-5-nitrobenzene were dissolved in DMF and heated with calcium carbonate to give, after tituration with isopropanol, 3-(2,6-dichloro-4-nitro-phenoxy)-quinoline (4) in 93% yield.

3,5-dichloro-4-(quinolin-3-yloxy)-phenylamine (5)

The nitro functionality of 3-(2,6-dichloro-4-nitro-phenoxy)-quinoline (4) was catalytically reduced under hydrogen with 5% weight/weight (catalyst/compound 4) of a 1% platinum/2% vanadium on carbon catalyst suspension in ethyl acetate at 0° C. The material was heated to 20° C., filtered through Celite. The Celite was washed with THF, and the filtrates were combined and evaporated to give 3,5-dichloro-4-(quinolin-3-yloxy)-phenylamine (5) in 98% yield.

2,4-dichloro-N-[3,5-dichloro-4-quinolin-3-yloxy) phenyl]-benzenesulfonamide HCl (1)

3,5-dichloro-4-(quinolin-3-yloxy)-phenylamine (5) was then reacted with 2,4-dichlorobenzenesulfonylchloride, followed by treatment with hydrochloric acid, to give 2,4-dichloro-N-[3,5-dichloro-4-quinolin-3-yloxy)phenyl]-benzenesulfonamide HCl (1; the hydrochloride salt of compound 101) in 99% yield.

7.8 Example 8

Preparation and Recrystallization of the Hydrochloride salt of Compound 101

This example describes a method that can be used to synthesize and recrystallize the hydrochloride salt of compound 101 from a precursor to compound 101. 3,5-Dichloro-4-(quinolin-3-yloxy)-phenylamine, prepared according to Example 7, in methylene chloride was treated with 2,4-dichlorobenzenesulfonylchloride and 2 equivalents of pyridine. The solution was concentrated by distillation of methylene chloride. After completion of the reaction the remaining solvent was removed under vacuum to yield a thick foam. The foam was re-dissolved in methylene chloride. Addition of 4 equivalents of 3N HCl gave a thick precipitate that was collected by filtration. The solids were washed with methylene chloride and then with water. After drying under vacuum, an amorphous solid was obtained. Carbon, Hydrogen, Nitrogen Combustion Analysis (CHN) indicated that the amorphous solid was the HCl salt of compound 101+0.5H$_2$O.

Further purification of the hydrochloride salt of compound 101 was obtained by conversion to the free base by extraction into ethyl acetate with NaHCO$_3$ solution. Drying with MgSO$_4$ and concentration gave the free base as a white solid. In this example, the free base of compound 101 was converted back to the hydrochloride salt. However, the procedures described in this example can be used to obtain any acid addition salt of compound 101 as described herein.

The free base of compound 101 (300 g) was suspended in ~3.5 L warm ethanol. NaOEt in ethanol (21%, ~240 mL) was added to form a complete solution. A solution of 145 mL of conc. HCl (~3 equivalents) in 450 mL of ethanol was added to the warm solution and the mixture was allowed to slow cool to room temperature. The solid precipitate was collected by vacuum filtration. The product was slurried in water (2 L) and recollected by filtration. After air drying, the product was dried under vacuum at 70° C. to constant weight of 311 g. The product was confirmed by NMR and CHN to be the anhydrous HCl salt of compound 101.

7.9 Example 9

Preparation of the Besylate Salt of Compound 101

The besylate salt of compound 101 was synthesized from 2,4-dichloro-N-[3,5-dichloro-4-quinolin-3-yloxy)phenyl]-benzenesulfonamide HCl prepared according to Example 7. The hydrochloride salt 2,4-dichloro-N-[3,5-dichloro-4-quinolin-3-yloxy)phenyl]-benzenesulfonamide HCl was converted to the besylate salt, via the free base, using a sodium bicarbonate/ethyl acetate biphasic reaction solution. Separation of the organic layer followed by solvent exchange with ethanol precipitated the besylate salt (6) of compound 101 in 84% yield. Starting from 4-aminoquinoline (2), the overall yield of the besylate salt (6) of compound 101 was 73%.

The preparation described in Examples 7 and 8 was performed two times; one batch yielded a mixture of Forms I and II of the besylate salt of compound 101. The other batch yielded only the Form II polymorph of the besylate salt of compound 101.

7.10 Example 10

Recrystallization of Form II of the Besylate Salt of Compound 101

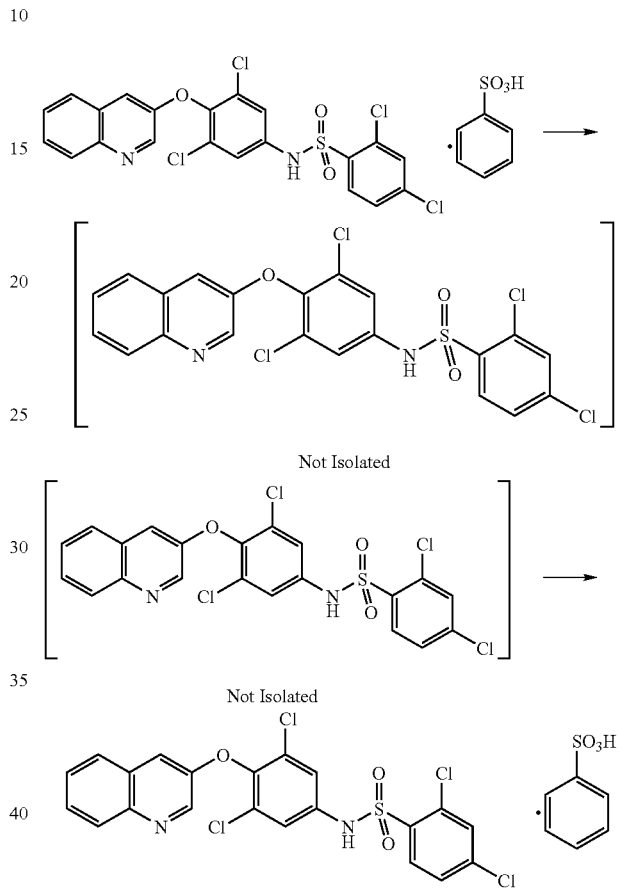

Compound 101 was recrystallized as Form II with benzenesulfonic acid (PhSO$_3$H-xH$_2$O; Aldrich).

A mixture of Forms I and II of the besylate salt (6) of compound 101 (6.938 kg), prepared according to Examples 7 and 8, was stirred in ethyl acetate (115 L) with gentle heating (about 28° C.). A saturated solution of sodium bicarbonate (13 L) was added in portions (endothermic, gas evolution). The biphasic mixture was stirred for approximately 1 hour. The phases were separated and the organic layer washed with a saturated sodium chloride solution (13 L). The organic layer was separated and concentrated by distillation (91 L distillate removed). Ethyl acetate (91 L) was added, the solution decolorized with activated charcoal, then filtered through Celite. The filter cake was washed with ethyl acetate (2×15 L) and the filtrates combined with the ethyl acetate filtrate from the activated charcoal decolorizing step. The solution was concentrated by distilling off approximately 135 L. Ethanol (16 L) was added and the solution heated to 77° C. Benzenesulfonic acid (4.126 kg) dissolved in ethanol (5 L) was added. An additional 2 L of ethanol was used to rinse the vessel containing the benzenesulfonic acid solution. After cooling to approximately 69° C., 36 g of besylate salt (6) of compound 101 was added. The suspension was stirred at approximately 67 to 69° C. for 38 minutes, then cooled to 20° C. and stirred for approximately 4 hours. 6.377 kg (92%) solid was obtained after filtering and drying under vacuum.

7.11 Example 11

Analysis of Form I

This example illustrates the differential scanning calorimetry (DSC) and hygroscopicity analysis of Form I prepared according to Example 6.

| Sample | DSC Melting Endotherm Maximum | FIG. |
|---|---|---|
| 1 | 189.5° C. | 4 |
| 2 | 188.4° C. | |
| 3 | 187.8° C. | |
| 4 | 188.2° C. | |

XRPD analysis of sample 1 (see FIG. 5) showed major peaks at approximately 7.0, 19.5, 24.0, 24.5 and 28.5° 2θ. Form I showed surprisingly low hygroscopicity with a weight gain of just 0.6% from 25% to 95% relative humidity and a weight loss of just 0.6% from 95% to 25% relative humidity (see FIG. 6).

7.12 Example 12

Analysis of Form I

This example illustrates the x-ray powder diffraction (XRPD) and differential scanning calorimetry (DSC) analysis of Form I prepared according to Example 8. The Form I polymorph of Example 8 showed similar properties to the Form I polymorph of Example 6.

| Sample | DSC Melting Endotherm Maximum |
|---|---|
| 5 | 186.3° C. |

XRPD analysis of sample 5 showed major peaks at approximately 7.0, 19.5, 22.0, 24.0, 24.5 and 28° 2θ. Scanning electron microscopy showed that Form I forms variable size, tabular particles with striations and possibly stacked sheets. Infrared spectra (see FIG. 7) showed Form I has peaks approximately 1567, 1461, 913, 895, and 881 $cm^{-1}$.

7.13 Example 13

Analysis of Form II

This example illustrates the differential scanning calorimetry (DSC) and hygroscopicity analysis of Form II prepared according to Example 8.

| Sample | DSC Melting Endotherm Maximum | FIG. |
|---|---|---|
| 6 | 233.7° C. | 8 |

XRPD analysis of sample 6 (see FIG. 9) showed major peaks at approximately 15, 19, 20.5, 23.5, 24.5, 25, 26.5, 29.5 and 30.5° 2θ. Infrared spectra (FIG. 10) showed Form II has peaks at approximately 1573, 1469, 1459, 912, and 859 $cm^{-1}$.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating Alzheimer's disease in a subject comprising administering to the subject a therapeutically effective amount of a benzenesulfonate salt of the compound of formula (I):

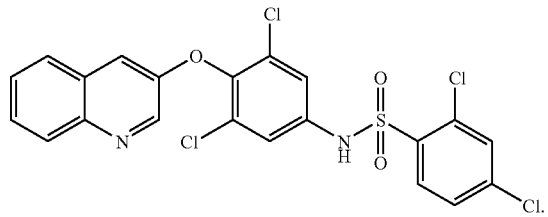

2. The method of claim 1, wherein the benzenesulfonate salt of the compound of formula (I) is in the form of a Form II polymorph, wherein the Form II polymorph has a melting point between about 230 and 240° C.

* * * * *